Figure 2A:
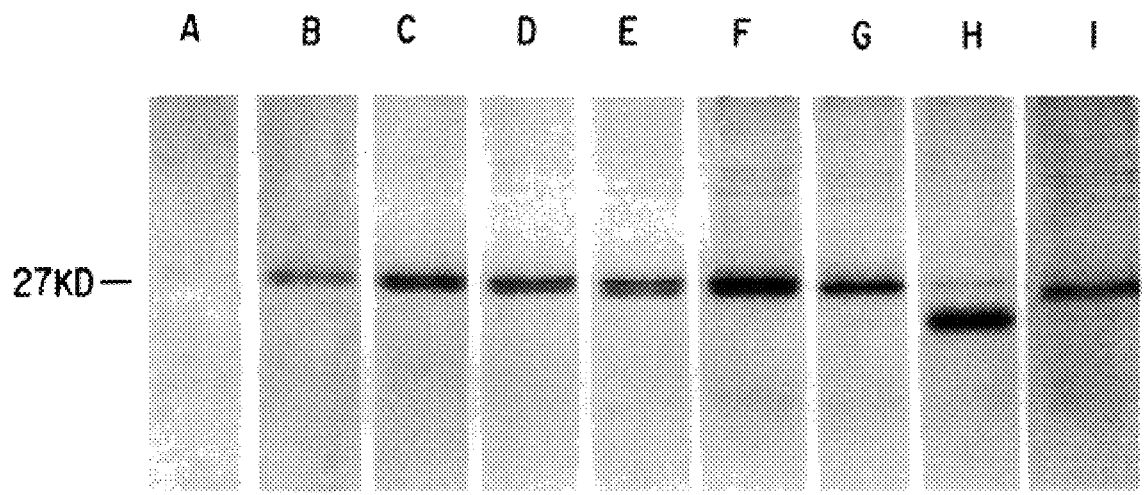

United States Patent [19]

Cullen

[11] Patent Number: 6,162,898
[45] Date of Patent: Dec. 19, 2000

[54] MUTANT REV TRANSDOMINANT REPRESSORS OF HIV REPLICATION

[75] Inventor: Bryan R. Cullen, Durham, N.C.

[73] Assignee: Duke University, Durham, N.C.

[21] Appl. No.: 09/138,069

[22] Filed: Aug. 21, 1998

Related U.S. Application Data

[62] Division of application No. 08/333,703, Nov. 3, 1994, Pat. No. 5,871,958, which is a continuation of application No. 08/042,379, Apr. 2, 1993, abandoned, which is a continuation of application No. 07/646,597, filed as application No. PCT/EP90/00831, May 23, 1990, abandoned, which is a continuation-in-part of application No. 07/442,670, Nov. 29, 1989, abandoned, and a continuation-in-part of application No. 07/356,878, May 25, 1989, abandoned.

[30] Foreign Application Priority Data

Jul. 7, 1989 [GB] United Kingdom ................... 8915602
Oct. 30, 1989 [GB] United Kingdom ................... 8924396

[51] Int. Cl.$^7$ .................................................. C07K 14/00
[52] U.S. Cl. ............................................................ 530/350
[58] Field of Search ........................... 530/350; 536/23.72

[56] References Cited

U.S. PATENT DOCUMENTS

| | | | |
|---|---|---|---|
| 4,738,922 | 4/1988 | Haseltine et al. | 435/69.3 |
| 4,935,372 | 6/1990 | Goh | 435/317.1 |
| 4,981,790 | 1/1991 | Haseltine et al. | 435/69.1 |
| 5,043,262 | 8/1991 | Haseltine et al. | 435/5 |
| 5,871,958 | 2/1999 | Cullen | 435/69.1 |

FOREIGN PATENT DOCUMENTS

| | | |
|---|---|---|
| 246882 | 11/1987 | European Pat. Off. |
| 291893 | 11/1988 | European Pat. Off. |
| 293181 | 11/1988 | European Pat. Off. |
| WO 87-07300 | 12/1987 | WIPO |
| WO 88-08454 | 11/1988 | WIPO |
| WO 89/11539 | 11/1989 | WIPO |
| WO 90/01266 | 2/1990 | WIPO |
| WO 90-01870 | 3/1990 | WIPO |
| WO 90/11359 | 10/1990 | WIPO |
| WO 90/13641 | 11/1990 | WIPO |
| WO 91/02805 | 6/1991 | WIPO |
| WO 91/10453 | 7/1991 | WIPO |

OTHER PUBLICATIONS

Arya et al., Science, 229:69–73 (1985).
Miller et al., The Operon, CHS, pp. 31–88 (1978).
Ptashne, M., Nature 335:683–89 (1988).
Ratner et al., Nature, 313:277–84 (1985).
Rosen et al., PNAS 85:2071–75 (1988).
Seiki et al., PNAS 80:3618–22 (1983).
Sodroski et al., Science, 229:74–77 (1985).
Sodroski et al., Science, 227:171–73(1985).
Abstract, 90–015165/02, USSH Aug. 8, 1998, U.S. Dept. Health and Human Services.
CA 114(i):3008s, Wong–Stall (1990), NTIS Order No. Pat–Appl–7–306–612.
Goh et al., Science, 227: 1227–1228 (1985).
Franza et al., The Control of Human Retrovirus Gene Expression, Cold Spring Harbor Laboratory, (1988).
Arrigo et al., J. Virol. 63, 4875–4881 (1989).
Baltimore, Nature 335, 395–396 (1988).
Chang et al., Science 249, 614–615 (1990).
Cochrane et al., J. Virol. 63, 4438–4440 (1989).
Cochrane et al., Virology 173, 335–337 (1989).
Cullen, Cell 46, 973–982 (1986).
Cullen, Meth. in Enzym. 152, 684–704 (1987).
Cullen et al., J. Virol. 62, 2498–2501 (1988).
Cullen, Nature 351, 698–699 (1991).
Culliton, Science 246, 746 (1989).
Daly et al., Nature 342, 816–819 (1989).
De et al., Nucleic Acids Res. 17, 2142 (1989).
Dokhelar et al., J.Acquir.Immune Defic.Synd. 2, 431–440 (1989).
Endo et al., Virus Genes 3, 99–110 (1989).
Feinberg et al., Cell 46, 807–817 (1986).
Felber et al., BIOSIS 37083067 (1989) (abstract only).
Friedman et al., Nature 335, 452–454 (1988).
Friedmann, Science 244, 1275–1281 (1989).
Green et al., Cell 58, 215–223 (1989).
Haigh et al., Nature 344, 257–259 (1990).
Hanly et al., Genes and Develop. 3, 1533–1544 (1989).
Haseltine, Scien.Amer., Oct. 1988, 52–62.
Hauber et al., J.Virol. 62, 4801–4804 (1988).
Herskowitz, Nature 329, 219–222 (1987).
Hidaka et al., EMBO J. 7, 519–523 (1988).
Hughes et al., J.Cell.Biochem.Supp. 13B, 276 (1989).
Itoh et al., Oncongene 4, 1275–1279 (1989).
Kubota et al., Biochem.Biophys.Res.Comm. 162, 963–970 (1989).
Lawson et al., Biotechnology 8, 127–134 (1990).
Lehn, Bone Marrow Transplant 1, 243–258 (1987).
Malim et al., Nature 335, 181–183 (1988).
Malim et al., Nature 338, 254–257 (1989).
Malim et al., Fifth Intl.Conf. on AIDS, Jun. 4–9, 1989 Montreal, Que., Canada.
Malim et al., Cell 58, 205–214 (1989).
Malim et al., Proc.Natl.Acad.Sci.USA 86, 8222–8226 (1989).
Malim et al., Cell 60, 675–683 (1990).
Manzari et al., Proc.Natl.Acad.Sci.USA 80, 1574–1578 (1983).

(List continued on next page.)

Primary Examiner—Remy Yucel
Attorney, Agent, or Firm—Diane E. Furman

[57] ABSTRACT

Transdominant repressors of viral gene phenotypic expression derived from the rev gene product of HIV-1 or the rex gene product of HTLV-1 and corresponding mutated genes, having the capability of repressing the Rev function in HIV-1 and/or the Rex function in HTLV-I and HTLV-II. And in some cases both the Rev and the Rex function and are, active in more than one viral species. Such transdominant viral mutants are useful as anti-viral agents to, for example of these transdominant inhibitors may be used in such therapeutic approaches as intracellular immunization in order to protect cells against the deleterious effects of viral, e.g. HIV-1, infection.

20 Claims, 26 Drawing Sheets

OTHER PUBLICATIONS

Mermer et al., Nucl.Acids Res. 18, 2037–2044 (1990).
Mitsuya et al., Science 249, 1533–1544 (1990).
Miyoshi et al., Nature 294, 770–771 (1981).
Newmark, Nature 342, 221 (1989).
Olsen et al., Science 247, 845–848 (1990).
Perkins et al., J.Acquir.Immune Defic.Syndr. 2, 256–263 (1989).
Peterlin et al., Biotechnology 6, 794–799 (1988).
Rimsky et al., Nature 341, 453–456 (1989).
Sadaie et al., Science 239, 910–913 (1988).
Seiki et al., Proc.Natl.Acad.Sci. USA 85, 7124–7128 (1988).
Siomi et al., Cell 55, 197–209 (1988).
Sodroski et al., Science 225, 381–385 (1984).
Sodroski et al., Nature 321, 412–417 (1986).
Staeheli, Tibtech 9, 71–72 (1991).
Tada et al., Proc.Natl.Acad.Sci. USA 87, 3479–3483 (1990).
Temin, Science, 246, 983 (1989).
Terwilliger et al., J.Virol. 62, 655–658 (1988).
Therre, Biofutur Mar. 1990, 21–22 (1990).
Trono et al., Cell 59, 113–120 (1989).
Wachsman et al., Science 235, 674–677 (1987).
Zapp et al., Nature 342, 714–716 (1989).
Zhou et al., Virus Genes 3, 153–158 (1989).
Amersham International plc, Oligonucleotide–directed in vitro mutagenesis system version 2, 1–32 (1988).
Scrip No. 1439, 23 (1989).
Scrip No. 1441, 18 (1989).
Scrip No. 1465, 21 (1989).
Rosenblatt et al., Science 240, 916–919 (1988).
Bahner et al., "Comparison of trans–Dominant Inhibitory Mutant Human Immunodeficiency Virus Type 1 Genes Expressed by Retroviral Vectors in Human T Lymphocytes", Journal of Virology, pp. 3199–3107 (Jun. 1993).
Bevec et al., "Inhibition of human immunodeficiency virus type 1 replication in human T cells by retroviral–mediated gene transfer of a dominant–negative Rev trans–activator", Proc.Natl.Acad.Sci. USA, vol. 89, pp. 9870–9874, (Oct. 1992).
Ferber et al., "Mechanism of function of the HIV–1 Rev protein", Int.Conf.AIDS, Jun. 20–23 (1990).
Fox et al., "Genetic Modification of Human Peripheral Blood Lymphocytes with a Transdominant Negative Form of Rev: Safety and Toxicity", Human Gene Therapy 6:997–1004 (Aug. 1995).
"Gene Therapy for AIDS," Scrip No. 2124, p. 19 (Apr. 30, 1996).
Green et al., "Mutational Analysis of HIV–1 Tat Minimal Domain Peptides: Identification of Trans–Dominant Mutants that Suppress HIV–LTR–Driven Gene Expression", Cell. vol. 58, 215–233, Jul. 14, 1989.
Malim et al., "Stable Expression of Transdominant Rev Protein in Human T Cells Inhibits Human Immunodeficiency Virus Replication", J.Exp.Med 176 pp. 1197–1201 (1992).
Malim et al., "Trans–Dominant Rev Mutants Can Protect T Cell Lines from HIV–1 Infection Without Disturbing Normal Function", J.Cell.Biochem.Suppl. 16E p. 33, Abstr. Q539 (1992).
Malim et al., "Transdominant Rev Protein Inhibits HIV Replication Without Affecting T Cell Function", Clin.Res. 40, Abstr., p. 253A (1992).
Mermer et al., "Identification of trans–dominant HIV–1 rev protein mutants by direct transfer of bacterially produced proteins into human cells", Nucleic Acids Research, vol. 18, No. 8, 2037.
Ragheb et al., "A Unified Gene Therapy Approach to the Treatment of AIDS," J.Cell Biochem.Suppl. 16E, p. 86, Abstract Q549 (1992).
Vandendriessche et al., "Inhibition of Clinical Human Immunodeficiency Virus (HIV) Type 1 isolates in Primary CD+T Lymphocytes by Retroviral Vectors Expressing Anti–HIV Genes," Journal of Virology, p. 4045–4052 (Jul. 1995).
Woffendin et al., "Expression of a protective gene prolongs survival of T cells in human immunodeficiency virus–infected patients", Proc.Natl.Acad.Sci. USA, vol. 93, pp. 2889–2894 (Apr. 1996).
Woffendin et al., "Nonviral and viral delivery of a human immunodeficiency virus protective gene into human T cells," Proc.Natl.Acad.Sci. USA, vol. 91, pp. 11581–11585 (Nov. 1994).
"Report and Recommendations of the Panel to Assess the NIH Investment in Research on Gene Therapy," Orkin and Motusky, Co–chairs, (Dec. 7, 1995).
Feinberg et al., AIDS Res.and Human Retrovir, 8(6):1013–1022 (1992).
Johnston et al., Science 260:1286–1293 (1993).
Gilboa et al., Trends in Genetics 10(4):139–144 (1994).
AIDS Agenda—Jun. 1996 (p. 6 (NIAID).
Rosenblatt et al., Science 240:916–919 (1988).
Rimsky et al., Nature 335:738–740 (1988).

```
  1  augcccaagacccgucgagggcccgccgauccccaagagaaaagaccuccaacaccauggcccacuucc      69
  1  METProLysThrArgArgArgProArgArgLysArgProThrProProThrProTrpProThrPro ThrSer  23

70  caggguuggacagagucuucuuuucgauaccccaguc uacguguuggagacuguguacaaggcgacu      138
 24  GlnGlyLeuAspArgVa lPhePheSerAspThrCysLeuGluThrVa lTyrLysAlaThr              46

139  ggugcccaucucugggggacuauguucgcccgccuacaucgucacgcccuacuggccaccuguccag          207
 47  GlyAlaProSerLeuGlyAspTyrValArgProAlaTyrI leVa lThrProTyrTrpProProVa lGln     69

208  agcaucagauccacccuggaccccaucgauggacgcguuauccggcucagcucuacaguuccuuaucccuc      276
 70  SerIleArgSerProGlyThrProSerMETAspAlaLeuSerAlaGlnLeuTyrSerSerLeuSerLeu        92
                                                                       87 88 89 90 91

277  gacucccuccucccaccagagaaccucaaggaccucuaggcuuaccccgccaaucaucacucaua            345
 93  AspSerProProSerProProArgGluProLeuArgProSerArgSerLeuProArgGlnSerLeuIle       115
       94                              97                                              82

346  caaccccccaacauuccaccuccuccuccaggccaugccaaaauacuccccuuccgaaauggauaca          414
116  GlnProProThrThrPheHi sProProSerSerArgProCysAlaAsnThrProProSerGluMETAspThr   138

415  uggaaccccaccucccuggggcagcaccuccaaccccuguccuuuuccagaccccggacuccggcccaaaacc    483
139  TrpAsnProProLeuGlyLeuGlySerThrSerGlnProCysLeuPheGlnThrProAspSerGlyProLysThr  161

484  uguacccucuggggaggcuccguugucugcauguaccucaccagucuuuccccccaucccuuccaccuggc      552
162  CysThrProSerGlyGluAlaProLeuSerAlaCysThrSerThrSerPheProProSerProProGly        184

553  cccucccugcccacg   567
185  ProSerCysProThr   189
```

A: pgtat (negative control for Rex antibody)
B: pcRex
C: pcRexM2
D: pcRexM7
E: pcRexM8
F: pcRexM13
G: pcRexM14
H: pcRexM17
I: pcRex13Δ15

A: pgtat + pXF3 + pXF3
B: pgtat + pcRex + pXF3
C: pgtat + pcRex + pcRexM2
D: pgtat + pcRex + pcRexM7
E: pgtat + pcRex + pcRexM8
F: pgtat + pcRex + pcRexM13
G: pgtat + pcRex + pcRexM14
H: pgtat + pcRex + pcRexM17
I: pgtat + pcRex + pcRex13Δ15

A: pgtat + pXF3 + pXF3
B: pgtat + pcRev + pXF3
C: pgtat + pcRev + pcRexM2
D: pgtat + pcRev + pcRexM7
E: pgtat + pcRev + pcRexM8
F: pgtat + pcRev + pcRexM13
G: pgtat + pcRev + pcRexM14
H: pgtat + pcRev + pcRexM17
I: pgtat + pcRev + pcRex13Δ15

| Mutant No. | Target sequence | Amino acid position No. | Mutant sequence |
| --- | --- | --- | --- |
| 1 | Thr-Ser | 22-23 | Asp-Leu |
| 2 | Phe-Phe-Ser | 30-31-32 | Leu-Asp-Leu |
| 3 | Gln-Ser | 35-36 | Asp-Leu |
| 4 | Glu-Thr | 40-41 | Asp-Leu |
| 5 | Pro-Ser | 49-50 | Asp-Leu |
| 6 | Tyr | 54 | Leu |
| 7 | Ala-Tyr | 58-59 | Asp-Leu |
| 8 | Pro-Tyr | 63-64 | Asp-Leu |
| 9 | Gln-Ser | 69-70 | Asp-Leu |
| 10 | Arg-Ser | 72-73 | Asp-Leu |
| 11 | Pro-Ser | 77-78 | Asp-Leu |
| 12 | Leu-Ser | 82-83 | Asp-Leu |
| 13 | Tyr-Ser-Ser | 87, 88, 89 | Leu-Asp-Leu |
| 14 | Leu-Ser | 90-91 | Asp-Leu |
| 15 | Ser | 94 | Leu |
| 16 | Pro-Ser | 96-97 | Asp-Leu |
| 17 | Arg-Glu | 100-101 | Asp-Leu |
| 18 | Ser-Arg-Ser | 106, 107, 108 | Leu-Asp-Leu |
| 19 | Gln-Ser | 112-113 | Asp-Leu |
| 20 | Ser-Ser | 124-125 | Asp-Leu |
| 21 | Pro-Ser | 133-134 | Asp-Leu |
| 22 | Ser-Thr-Ser | 145, 146, 147 | Gly-Asp-Leu |
| 23 | Ser | 157 | Leu |
| 24 | Pro-Ser | 164-165 | Asp-Leu |
| 25 | Gly-Glu | 166-167 | Asp-Leu |
| 26 | Leu-Ser | 170-171 | Asp-Leu |
| 27 | Ser-Thr-Ser | 175, 176, 177 | Leu-Asp-Leu |
| 28 | Pro-Ser | 181-182 | Asp-Leu |
| 29 | Pro-Ser | 185-186 | Asp-Leu |

FIG.3

| | |
|---|---|
| # 1: | CA ACA CCA TGG CCA GAT CTC CAG GGT TTG GAC |
| # 2: | TG GAC AGA GTC TTA GAT CTG GAT ACC CAG TCT |
| # 3: | TC TTT TCG GAT ACA GAT CTT ACG TGT TTG GAG |
| # 4: | AG TCT ACG TGT TTA GAT CTT GTG TAC AAG GCG |
| # 5: | AG GCG ACT GGT GCA GAT CTT CTG GGG GAC TAT |
| # 6: | CC CCA TCT CTG GGA GAT CTT GTT CGG CCC GCC |
| # 7: | AC TAT GTT CGG CCA GAT CTC ATC GTC ACG CCC |
| # 8: | CC TAC ATC GTC ACA GAT CTC TGG CCA CCT GTC |
| # 9: | AC TGG CCA CCT GTA GAT CTC ATC AGA TCA CCT |
| # 10: | CT GTC CAG AGC ATA GAT CTA CCT GGG ACC CCA |
| # 11: | GA TCA CCT GGG ACA GAT CTG ATG GAC GCG TTA |
| # 12: | CA TCG ATG GAC GCA GAT CTG GCT CAG CTC TAC |
| # 13: | TCG GCT CAG CTC TTA GAT CTC TTA TCC CTC GA |
| # 14: | AG CTC TAC AGT TCA GAT CTC CTC GAC TCC CCT |
| # 15: | GT TCC TTA TCC CTA GAT CTC CCT CCT TCC CCA |
| # 16: | CC CTC GAC TCC CCA GAT CTC CCA CCC AGA GAA |
| # 17: | CT CCT TCC CCA CCA GAT CTA CCT CTA AGA CCC |
| # 18: | CCT CTA AGA CCC TTA GAT CTC TTA CCC CGC CA |
| # 19: | GG TCC TTA CCC CGA GAT CTA CTC ATA CAA CCC |
| # 20: | CA TTC CAC CCT CCA GAT CTC AGG CCA TGC GCA |
| # 21: | GC GCA AAT ACT CCA GAT CTC GAA ATG GAT ACA |
| # 22: | CA CCC TTG GGC GGA GAT CTC CAA CCC TGT CTT |
| # 23: | TT TTC CAG ACC CCA GAT CTC GGC CCC AAA ACC |
| # 24: | CC AAA ACC TGT ACA GAT CTT GGG GAG GCT CCG |
| # 25: | CC TGT ACA CCC TCA GAT CTG GCT CCG TTG TCT |
| # 26: | CT GGG GAG GCT CCA GAT CTT GCA TGT ACC TCT |
| # 27: | CT GCA TGT ACC TTA GAT CTC TTT CCC CCC CCA |
| # 28: | CC AGC TTT CCC CCA GAT CTA CCT GGC CCC TCC |
| # 29: | CC CCA TCA CCT GGA GAT CTC TGC CCC ACG TGA |

```
                  67                    78       83  86       92              116
         Mutant   S A E P V P L Q L P P L E R L T L D C N E D C G T S . . . . . . . . . S G A K E
         pM15                         D L
         pM16                           D L
         pM17                             D L
         pM18                               D
         pM19                               D L
         pM20                                   D L
         pM21                                     D L
         pM22                                       D L
         pM23                                       E D L
         pM24                                       K D L
         pM25                                       E D L
         p 9/19   D - - - - - -
         p 18/19                       D - -
         p 18/23                       D - - - - - - - L
         p 22/14                                         D - - - - - - . . . . . . . . . . . L
         p 23/14                                       E D - - - - - - . . . . . . . . . . . L
         pM27                                   A
         pM28                                       A
         pM29                                 A         A
         pM32                                   A       A
         pM33                                             N
         pM34                                             S
         pM35                             Q               V
         pM36                             V
```

1
atggcaggaagaagcggagacagcgacgaagacctcctcaaggcagtcagactcatcaagtttctctat
METAlaGlyArgSerGlyAspSerAspGluAspLeuLeuLysAlaValArgLeuIleLysPheLeuTyr 70
caaagcaaccacctcccaatcccgaggggacagcccgaaggaatagaagaagaagaaggtggaga
GlnSerAsnProProProAsnProGluGlyThrArgGlnAlaArgArgAsnArgArgArgArgTrpArg 139
gagagacagagacagatccattgattagtgaacggatcctagcacttatctgggacgatctgcggag
GluArgGlnArgGlnIleHisSerIleSerGluArgIleLeuSerThrTyrLeuGlyArgSerAlaGlu 208
cctgtgcctcttcagctaccaccgcttgagagacttactcttgattgtaacgagattgtgaacttct
ProValProLeuGlnLeuProProLeuGluArgLeuThrLeuAspCysAsnGluAspCysGlyThrSer 277
gggacgcaggggtgggaagccctcaaatattggtggaatctcctacagtattggagtcaggagctaaa
GlyThrGlnGlyValGlySerProGlnIleLeuValGluSerProThrValLeuGluSerGlyAlaLys 346
gaatag
Glu

FIG. 6

M1   CCT ATG GCA GGA GAT CTC GGA GAC AGC GA

M2   GA AGA AGC GGA GAA GAT CTC GAA GAC CTC CTC

M3   C CTC AAG GCA GTA GAT CTC ATC AAG TTT C

M4   AG TTT CTC GAT CAA GAT CTC CCA CCT CCC A

M5   G ACC CGA CAG GCA GAT CTG AAT AGA AGA AG

M6   G GCC CGA AGG AAA GAT CTG TGG AGA GAG AGA C

M7   G AGA CAG ATC CAT ATT GAA CGG ATC CTT AGC

M8   GT GAA CGG ATC CTA GAT CTT TAT CTG GGA CC

M9   TAT CTG GGA CGA GAT CTG GAG CCT GTG CC

M10  CAG CTA CCA CCA GAT CTG AGA CTT ACT CTT

M11  GAG GAT TGT GGA GAT CTT GGG ACG CAG GG

M12  CAG GGG GTG GGA GAT CTT CAA ATA TTG GTC

M13  CAA ATA TTG GTG GAA GAT CTT ACA GTA TTG GAG

M14  CT ACA GTA TTG GAA GAT CTA GCT AAA GAA TAG

FIG.7

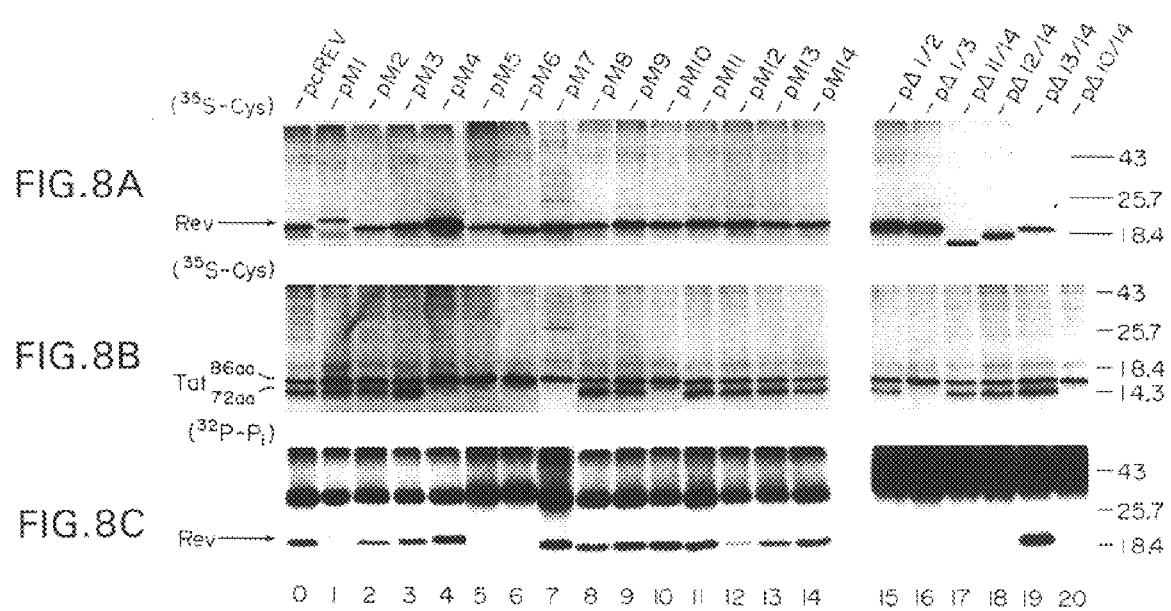

N

N

N>C

N≥C

C>N

```
           M21  M1                   M22   M2                          M23   M24 M25 M26        M3        M4  M27   40
    1      M P K [T R R R] P R R S [S Q S K] R P P T P [W] P [T S Q G L] D R V [F F] S [D T Q S T] C L E

M5                                  M6    M7            M8                                     80
    41     T V [Y K] A T G A P S L G D Y V R P A [Y I] V T P [Y W] P P V Q S I [R S] P G T P S M D
                                                                                                         120
           M9                        M10              M11              M12                   M13
    81     A L S A Q L [Y S S] L S L D S P P P S P P R [E P] L R P S [R S] L [P R Q S] L I Q P P [T F]

M14                              M15                      M16                     160
    121    [H] P P S S R P C A N T P P [S E M] D T W N P P [L G] S T S Q P C L F Q T P [D S G] P K

189
           M17                                        M18
    161  T [C T] P S G E A P L S A C T S T S F P P P [S P] G P S C P T
```

FIG. 13A

MUTANT REV TRANSDOMINANT REPRESSORS OF HIV REPLICATION

This application is a division of application Ser. No. 08/333,703 filed Nov. 3, 1994, now U.S. Pat. No. 5,871,958, which is a continuation of application Ser. No. 08/042,379 filed Apr. 2, 1993, now abandoned, which in turn is a continuation of application Ser. No. 07/646,597 filed Jun. 26, 1991, now abandoned, which is a 371 of PCT/EP90/00831 filed May 23, 1990, which in turn is a continuation-in-part of application Ser. No. 07/442,670 filed Nov. 29, 1989, now abandoned, and a continuation-in-part of application Ser. No. 07/356,878 filed May 25, 1989, now abandoned.

1. FIELD

The invention concerns the field of viral gene expression, more particularly the phenotypic expression of the rex (regulator of virion-protein expression) gene of HTLV-I and its equivalents in other retroviral species, such as rev of HIV-1.

2. BACKGROUND

Viruses, particularly human retroviruses like the human immunodeficiency virus type 1 (HIV-1) or the human leukemia virus type I (HTLV-I), are the causative agents for very serious diseases. This is in the case of HIV-1 the Acquired Immune Deficiency Syndrome (AIDS) and in the case of HTLV-I Adult T-cell Leukemia (ATL) as well as noncancerous conditions known as Tropical Spastic Parapesis. HTLV-II is etiologically related to some cases of variant T-cell hairy cell leukemia. Both virus groups are dividing their replication cycle, similarly to the DNA viruses, in an "early" and a "late" stage of gene expression. The "early" phase of gene expression is characterized by the expression of the regulatory proteins, while in the "late" phase the structural proteins are synthesized.

The HTLV-I genome is coding for an activator of viral transcription termed Tax. The equivalent of Tax in HIV-1 is termed Tat. Tax and Tat appear to act primarily on the retroviral LTR (long terminal repeat) for viral gene expression. In addition, HTLV-I encodes an activator of viral structural gene expression termed Rex. A functional Rex protein is responsible for the increased transport of unspliced viral mRNA out of the nucleus into the cytoplasm of the infected cell. There these mRNA species are constituting the viral genome and encoding the structural proteins. Human Immunodeficiency Virus Type 1 (HIV-1) encodes a homologous protein termed Rev. The rev gene product is, as Rex in the HTLV-I system, absolutely required for the expression of the HIV-1 structural proteins.

The underlying reason for this is that the product of the rev gene (and its equivalents in other viral species) is having a dramatic effect on the selection of the splicing mode for the viral mRNA transcripts in infected cells. This effect is achieved in the case of Rev and Rex by posttranscriptional regulation, namely by enhancement of the transport into the cytoplasm of full-length mRNA transcripts, whereby expression of viral structural proteins such as Gag and Env for HIV-1 is initiated and expression of regulatory proteins is concomitantly suppressed (see e.g. for Rex M. Hidaka et al., *EMBO J.* 7 [1988] 519) or modulated (see e.g. for Rev M. H. Malim et al., *Nature* 335 [1988] 181). Thus Rev is not required for the expression of the fully spliced HIV-1 mRNAs encoding the viral regulatory proteins, including Tat and Rev.

In HIV-1 the selectivity of the induction noted above is due to an RNA target sequence required for Rev function termed Rev Response Element (RRE). RRE coincides with a large, 234 nucleotide RNA secondary structure present within the HIV-1 env gene. The equivalent structure in HTLV-I is termed Rex Response Element (RexRE or RRX). Rev appears to be the first protein which has been shown to regulate the nuclear export of RNA in a sequence specific manner.

Taking Rex as an illustration, the complete function of the Rex protein in regulating expression of the HTLV-I gag and env genes requires at least three functionally distinct component activities: nuclear and nucleolar localization, i.e. the capacity to be transported from the cytoplasmic site of synthesis of all proteins to the nucleus and there to be concentrated in the nucleolar region; specific recognition (directly or indirectly) of the RexRE (RRX) sequence in viral RNAs; and Rex effector activity, the presently still unknown activity of this regulatory protein which actually mediates export from the nucleus to the cytoplasm of partially spliced viral mRNA species that include the RexRE sequence.

Regarding the structural locations in the Rex protein where these component activities of the complete Rex function reside (i.e. the functional domains), all that was known prior to the present invention is that a positively charged peptide domain in the first twenty amino acids at the amino terminus of Rex is required for nucleolar localization (H. Siomi et al., *Cell* 55 [1988] 197–209).

As mentioned above both the rex gene product for HTLV-I and the rev gene product for HIV-1 are required for replication of the virus (see e.g. for HIV E. Terwilliger et al., *J. Virol.* 62, [1988] 655). The crucial importance of Rex and Rev is underscored by the fact that in spite of their different primary structures, they are related functionally, and HTLV-I Rex is able to exert its function in the other viral species, i.e. in HIV-1 (L. Rimsky et al., *Nature* 335 [1988] 738): thus even though Rev and Rex do not share any significant homology on the nucleotide as well as on the amino acid level, the nucleotide sequences and stem and loop structures of the RRE differ from those of the RexRE (RRX) in HTLV-I, computer-generated prediction of secondary structures of the Rex and Rev proteins reveal no significant similarities and the Rex protein does not appear to bind to the same part of the RRE as the Rev protein does, it is nevertheless possible to substitute the Rev protein by the Rex protein in the HIV-1 system, and further, it has very recently been found that HTLV-I Rex and HIV-1 Rev can substitute for HIV-2 Rev (Rev2) and that HTLV-I Rex can also substitute for the analogous HTLV-II regulatory protein. This complementation is sufficient to rescue e.g. a rev-deficient HIV-1 provirus providing functional Rex protein in trans. On the other hand the reverse substitution to rescue a rex-deficient HTLV-I provirus by functional Rev protein does not seem to be feasible. Thus there is no complete symmetry in this respect. The basis for this lack of reciprocality is not yet understood, but it probably relates to differences in the functional aspects of these proteins that are required for target RNA sequence recognition.

Mutations in regulatory proteins may yield a gene product with a dominant negative phenotype over the wild-type function (I. Herskowitz, *Nature* 329 [1987] 317). Dominant negative mutant proteins, known as trans-dominant repressors, a small group of which have been discovered recently in several unrelated viruses, represent a novel class of anti-viral agents. In genetic analyses, negative mutations are those which cause a diminution or loss of a function of a gene. Dominant negative mutations are those that prevent other copies of the same gene, which have not been mutated (i.e. which have the wild-type sequence), from functioning properly. On the other hand recessive negative mutations do not so inhibit wild-type counterparts. Further, some dominant mutations inhibit wild-type genes only when the mutant and wild-type genes are located on the same chromosome (DNA or RNA molecule). In this case the inhibiting mutation is said to be "cis-acting". Alternatively, a dominant mutation may inhibit the corresponding wild-type gene even when located on a separate chromosome. This type is classified as a "trans-acting" dominant mutation or, more simply, as a transdominant mutation.

A few of these so-called transdominant genes have been described, concerning genes for eukaryotic or Herpes virus transcription factors (I. A. Hope and K. Struhl, *Cell* 46 [1986] 885; R. Gentz et al., *Science* 243 [1989] 1695; S. J. Triezenberg et al., *Gen. & Devel.* 2 [1988] 718; A. D. Friedman et al., *Nature* 335 [1988] 452). Thus, when overexpressed some deletion mutants of the Herpes simplex virus trans-activator VP16 inhibit VP16 function, thereby precluding replication of HSV-1 in normally permissive cells. As regards retroviruses, transdominant mutants have also been described, e.g. for the Tax protein of HTLV-II (W. Wachsman et al., *Science* 235 [1987] 674) and, after the priority date for the present invention, for the HIV-1 tat (M. Green et al., *Cell* 58 [1989] 215) and gag (D. Trono et al., *Cell* 59 [1989] 113) genes.

These differences in compositions and functions of these two regulatory proteins indicate that comparison of Rex structure with that of the Rev protein or its known mutants offers no guidance at all for selecting mutations that might produce trans-dominant repressors of the viral proteins.

A therapeutic application of the above concepts would involve the inhibition of production or overproduction of a deleterious gene product by manipulation of the gene to create dominant negative mutations whereby the resultant gene is encoding mutant regulatory proteins which when expressed disrupt the activity of the wild-type function (I. Herskowitz, *Nature* 329 [1987] 219). In the situation of viral, e.g. retroviral, infections it thus appears highly desirable to provide corresponding transdominant repressors of virus function by the construction of similar inhibitors of essential regulatory genes, e.g. inhibitors of the rev or rex gene. This approach would provide the requisite tools for "intracellular immunization", an approach to the treatment of viral infections first proposed in 1988 (D. Baltimore, *Nature* 335 [1988] 395).

3. SUMMARY OF THE INVENTION

Engineered transdominant versions of the HTLV-I rex and, respectively, of the HIV-1 rev gene have now been made, the product of which blocks HTLV-I, HTLV-II or, respectively, HIV-1 replication. Furthermore, the product of some of these engineered transdominant versions of the rex or rev gene blocks both HTLV-I (and in some instances HTLV-II) and HIV-1 (and in some instances HIV-2 and SIV) replication.

This appears to be the first reported occurrence of the preparation of viral repressors acting in more than one viral species, i.e. of transdominant gene products repressing the phenotypic expression of functionally equivalent genes of more than one viral species.

The invention thus concerns genes coding for proteins which transdominantly repress the phenotypic expression of functionally equivalent genes of more than one viral species and thus block replication of more than one viral species, particularly the mutant genes in pcRexM2, pcRexM7 and pcRexM8; M6, M7 and M13; and pM10, disclosed hereunder.

It also concerns genes coding for proteins which transdominantly repress the phenotypic expression of the rex gene of HTLV-I and/or HTLV-II and genes coding for proteins which transdominantly repress the phenotypic expression of the rev gene of HIV-1 and/or HIV-2 and/or SIV, particularly the mutant genes in pcRexM2, pcRexM7, pcRexM8, pcRexM17 and pcRex13Δ15; pM10, pΔ9/14, pΔ10/14, pM21, pM22, pM27, pM28, pM29 and pM32; and M6, M7 and M13, disclosed hereunder.

It also concerns a process for the preparation of these genes comprising isolating the corresponding wild-type gene from an appropriate expression system, putting this gene into an appropriate cloning system, introducing the desired mutation into the gene and recovering the resultant mutant gene from the clones having the desired mutation. It also concerns a process for the preparation of proteins as defined above which comprises expressing and amplifying a mutant gene as defined above in an appropriate expression and amplification system and recovering the expressed product therefrom.

It also concerns proteins which transdominantly repress the phenotypic expression of functionally equivalent genes of more than one viral species and thus block replication of more than one viral species, in particular the mutant proteins of pcRexM2, pcRexM7 and pcRexM8; M6, M7 and M13; and pM10, disclosed hereunder.

It also concerns proteins which transdominantly repress the phenotypic expression of the rex gene of HTLV-I and/or HTLV-II, and proteins which transdominantly repress the phenotypic expression of the rev gene of HIV-1 and/or HIV-2 and/or SIV, in particular the mutant proteins of pcRexM2, pcRexM7, pcRexM8, pcRexM17 and pcRex13Δ15; pM10, pΔ9/14, pΔ10/14, pM21, pM22, pM27, pM28, pM29 and pM32; and M6, M7 and M13, disclosed hereunder.

It also concerns a vector, e.g. a retroviral or plasmid vector, containing a gene as defined above in a form suitable for achieving delivery in a functional state into a target mammalian cell in vivo or in vitro.

It also concerns a pharmaceutical composition containing a gene or protein as defined above in a form suitable for achieving the desired prophylactic or therapeutic effect, together with a pharmaceutically acceptable carrier or diluent, e.g. in the form of cells taken from a patients's body and treated in vitro prior to reinsertion.

It also concerns a method of treatment of viral infections comprising administering a gene or protein as defined above in a form suitable for achieving the desired prophylactic or therapeutic effect to a subject in need of such treatment, e.g. in the form of cells taken from a patient's body and treated in vitro prior to reinsertion.

Under "treatment" is to be understood the prophylactic as well as the curative treatment of viral infections, whereby "curative" includes the stabilization of a viral infection at a stage of latency.

It also concerns the genes, proteins and DNA segments defined herein for use as a pharmaceutical.

The invention also concerns the genes and proteins defined above in the form of functional fragments or derivatives, i.e. fragments or derivatives which are functionally equivalent. Under "functional fragment or derivative" is to be understood a fragment or derivative having a pharmacological activity which is qualitatively identical with the pharmacological activity of the intact mutant gene or protein and is quantitatively the same or different, i.e. either greater or smaller, than the pharmacological activity of the intact mutant gene or protein, e.g. from about 1% to about 10000%, particularly from about 10% to about 1000%.

The invention also concerns inhibitors derived from the genes, proteins and DNA segments defined herein and able to mimic the transdominant, i.e. primarily the RNA-binding domain in a mutant Rex or Rev protein as defined above, such as low molecular weight inhibitors or neutralizing monoclonal antibodies. Low molecular weight means herein a molecular weight below about 10 kD, especially below about 1 kD.

Further aspects which the invention concerns are as listed hereunder:

A trans-dominant repressor of HIV-1 Rev function comprising a first and a second domain, the first domain having substantially the specific binding functions of wild-type HIV-1 Rev and the second domain not having the activation functions of wild-type HIV-1 Rev, the second domain being modified from wild-type HIV-1 Rev by one or more mutations; preferably the first domain comprises from about amino acid position 10 to about amino acid position 68 of wild-type Rev and the modified second domain is derived from about amino acid position 68 to about amino acid position 90 of wild-type Rev; especially, the above one or more mutations are missense or deletion mutations which occur between about amino acid position 68 and about amino acid position 90, preferably from about 78 to about 86, especially from about 78 to about 83 or 84 of wild-type Rev, the specific binding functions of the first domain of wild-type HIV-1 Rev remaining substantially functionally intact; particularly the repressors pM10, pM21, pM22, pM27, pM28, pM29 and pM32 disclosed hereunder or a functional fragment or derivative thereof;

a trans-dominant repressor of HIV-1 Rev function comprising a first domain having substantially the specific binding functions of wild-type HIV-1 Rev, this transdominant repressor not having the activation functions of wild-type HIV-1 Rev; preferably the first domain comprises from about amino acid position 10 to about amino acid position 68 of wild-type Rev and the transdominant repressor lacks from about amino acid position 68 to at least about amino acid position 90 of wild-type Rev; particularly the repressors pΔ9/14 and pΔ10/14 disclosed hereunder or a functional fragment or derivative thereof;

a DNA segment that encodes a trans-dominant repressor of the function of the HTLV-I Rex protein, the repressor being modified from a wild-type form of the Rex protein by at least one trans-dominant negative mutation in the peptide domain of the wild-type Rex protein that exhibits the effector activity of the Rex protein, this repressor having substantially the nucleolar localization activity of the wild-type form of the Rex protein; preferably such a DNA segment in which the peptide domain of the wild-type Rex protein comprises from about amino acid position 59 to about amino acid position 121, especially in any one of the following amino acid positions: 59, 60, 64, 65, 119, 120 and 121; particularly a DNA segment comprising any of the following mutant rex genes: M6, M7, M13 and variants and derivatives thereof which exhibit transdominant repression of HTLV-I Rex protein function;

a corresponding trans-dominant repressor of the function of the HTLV-I Rex protein so modified from a wild-type form, preferably having the ability to repress either the function of the HIV-1 Rev protein or the function of the HTLV-II Rex protein;

a method for identifying a specific inhibitor of the gene activation function of the Rex protein comprising the steps of:
  i) providing a genetic system comprising:
    a DNA segment encoding an mRNA which comprises a regulatory response element that is recognized by the Rex protein, and at least one unused splice site (i.e. a region or intron that is bounded by splice recognition sequences but that has not been spliced out of the mRNA);
    a DNA segment encoding a rex gene that is capable of being expressed to produce a protein product which induces export of the mRNA from the nucleus;
    a host cell transformed by the DNA segment encoding the rex gene and by the DNA segment encoding the mRNA and having the capability to express the protein product of the rex gene and to express the mRNA;
  ii) contacting a culture comprising the cells of this genetic system with an agent suspected of being a specific inhibitor of the Rex protein under conditions such that the agent enters the cells;
  iii) determining the effect of this agent on export from the nucleus of the mRNA that comprises the unused splice site; and
  iv) determining the effect of the agent on export from the nucleus of a spliced form of the mRNA in which the splice site has been used;
whereby a decrease in the export of the mRNA that comprises the unused splice site together with no decrease in the export of the spliced form of the mRNA indicates that the agent is a specific inhibitor of an activity of the HTLV-I rex gene or of an activity of a product of the rex gene; the mRNA regulatory element that is recognized by the Rex protein preferably being derived from an mRNA of a virus selected from HTLV-I, HTLV-II and HIV-1;

an identification method as defined above wherein the decrease in the export of the mRNA that comprises the unused splice site is preferably detected by determining the level of production of a first protein, encoded by the mRNA that comprises the unused splice site, and the increase in export of the spliced form of the mRNA is preferably detected by determining the level of production of a second protein, encoded by the spliced form of the mRNA;

an identification method as defined above wherein the mRNA comprising the regulatory response element and the splice site is encoded by a plasmid comprising the 3' end of an HTLV-I provirus including the coding regions for the Rex and Tax proteins, the complete env gene, the Rex response element and the entire 3' LTR; preferably by plasmid pgTAX-LTR disclosed hereunder; and the rex gene preferably is provided on plasmid pRex;

plasmid pgTAX-LTR;

a reagent kit for screening agents to identify a specific inhibitor of the gene activation function of the Rex protein according to the above identification method, comprising:
  a DNA segment encoding an mRNA which comprises a regulatory response element that is recognized by the Rex protein, and at least one unused splice site;
  a DNA segment encoding a rex gene that is capable of being expressed to produce a protein product which induces export of the mRNA from the nucleus; and a container containing a host cell transformed by the DNA segment encoding the rex gene and by the DNA segment encoding the mRNA, the cell having the capability to express the protein product of the rex gene and the mRNA;

a method of inhibiting replication of HIV-1, HTLV-I or HTLV-II comprising introducing a DNA segment as defined above into a cell having the ability to replicate one of these viruses and to express the DNA segment to produce a transdominant repressor of HTLV-I Rex function; and a method of inhibiting HIV-1, HIV-2 and SIV, especially HIV-1, replication comprising introducing into a cell infected with HIV-1 a trans-dominant repressor of HIV-1 Rev function.

4. EXPLANATION OF THE FIGURES 4.1. for 5.1. and 6.1.

Figure 1A:
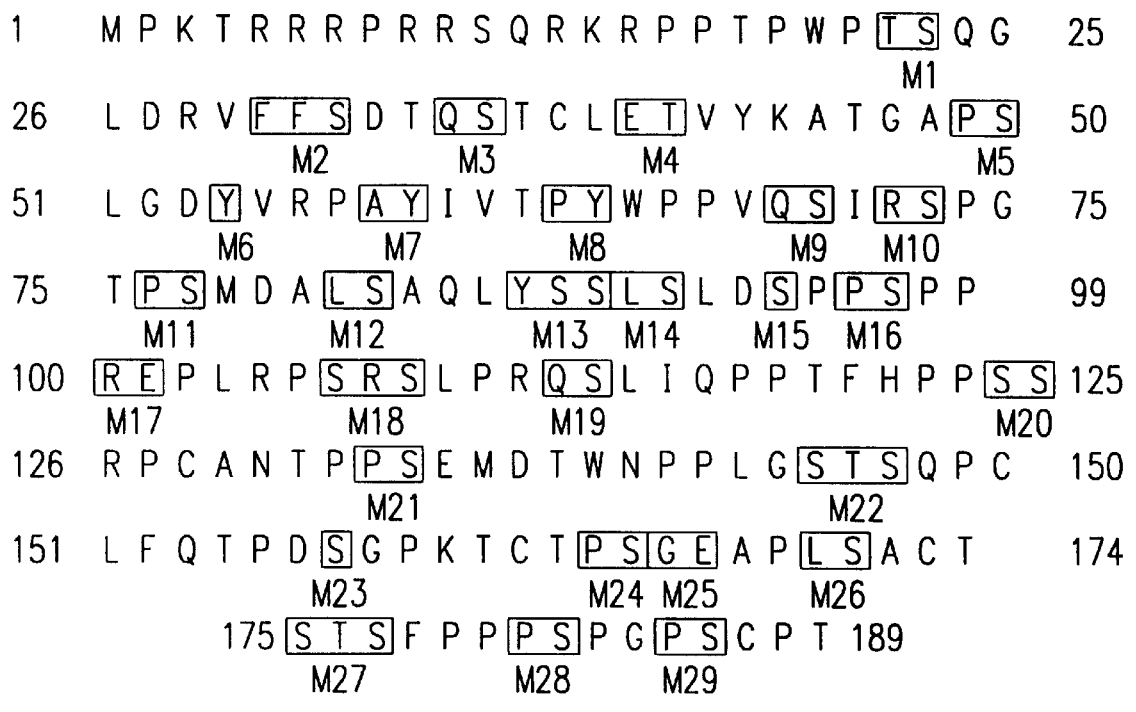

FIG. 1: Nucleotide and amino acid sequence of HTLV-I rex [the amino acid positions substituted by oligonucleotides (1) (amino acid positions 87, 88, 89) and (2) (position 94) are marked, as well as positions 82, 90, 91 and 97. The full sequence contains 567 nucleotides, coding for 189 amino acids.

FIG. 1A: Location of the 29 mutations introduced into the HTLV-I rex gene. The HTLV-I rex gene encodes a 189 amino acid protein. Using site-directed mutagenesis, missense substitutions were introduced at defined amino acid residues (indicated by boxes) and are named according to their location within the rex gene.

FIG. 2A: Rex immunoprecipitation:
SDS/polyacrylamide gel electrophoretic analysis of 7 of the 30 rex mutants after Rex immunoprecipitation (shows that pcRexM2, pcRexM7, pcRexM8, pcRexM13, pcRexM14, pcRexM17 and pcRex13Δ15 are still producing Rex protein):
A: pgtat (negative control for Rex antibody)
B: pcRex
C: pcRexM2
D: pcRexM7
E: pcRexM8
F: pcRexM13
G: pcRexM14
H: pcRexM17 (the lower molecular weight in this lane is possibly due to a change in the modification of this protein by, e.g., phosphorylation)
I: pcRex13Δ15

Figure 2B:
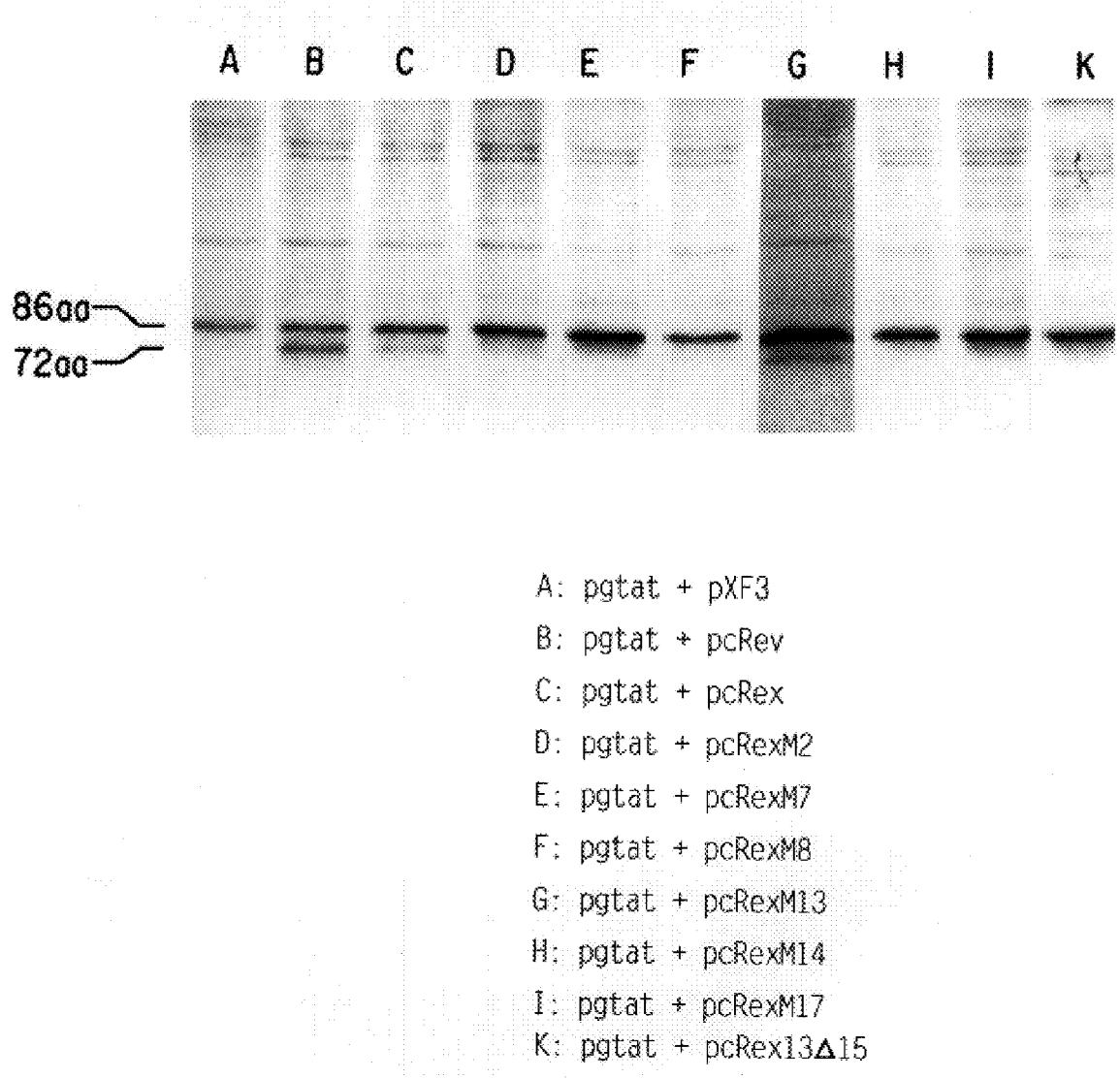

FIG. 2B: Biological phenotype of the mutants:
As for FIG. 2A, after Tat immunoprecipitation:
A: pgtat+pXF3
B: pgtat+pcRev
C: pgtat+pcRex
D: pgtat+pcRexM2
E: pgtat+pcRexM7
F: pgtat+pcRexM8
G: pgtat+pcRexM13
H: pgtat+pcRexM14
I: pgtat+pcRexM17
K: pgtat+pcRex13Δ15

Figure 2C:
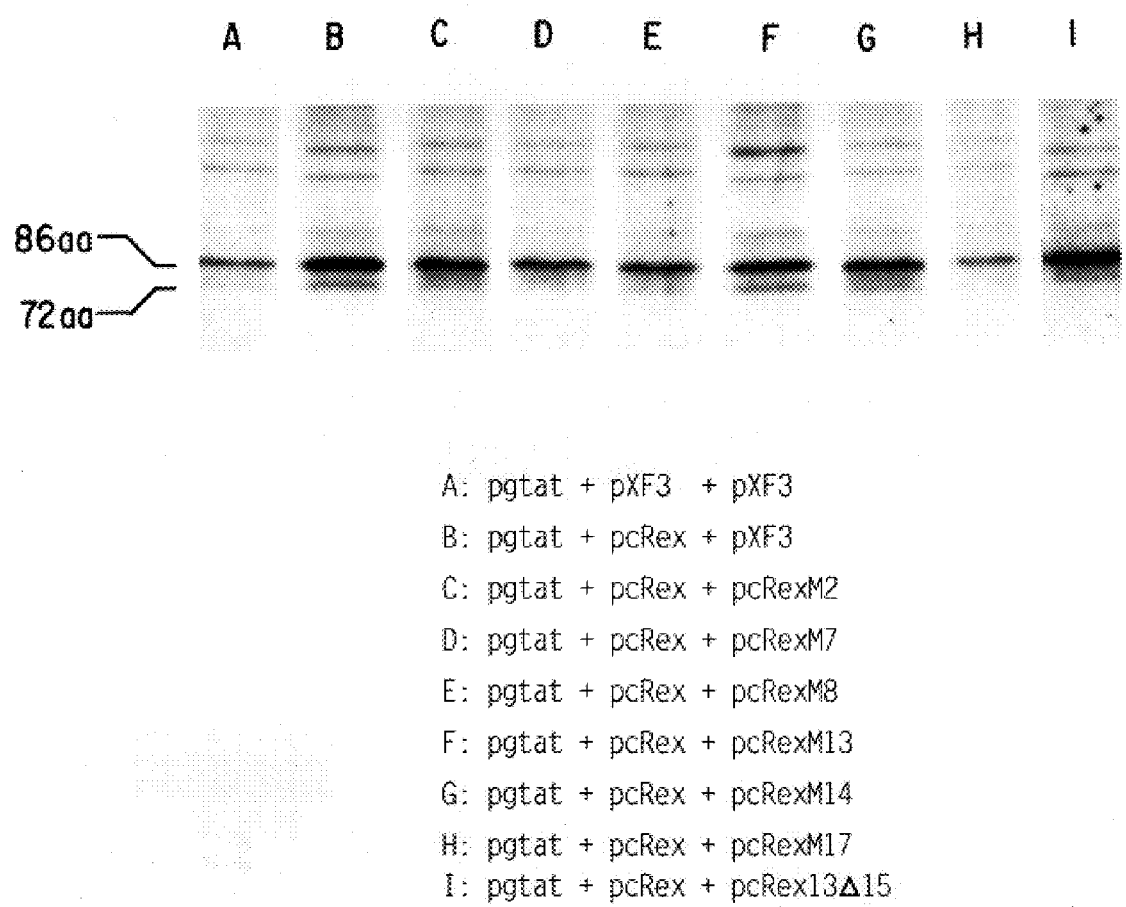

FIG. 2C: As for FIG. 2B (shows that some of the Rex mutants are transdominant over wildtype Rex, namely pcRexM2, pcRexM7, pcRexM8, pcRexM14, pcRexM17 and pcRex13Δ15):
A: pgtat+pXF3+pXF3
B: pgtat+pcRex+pXF3
C: pgtat+pcRex+pcRexM2
D: pgtat+pcrex+pcRexM7
E: pgtat+pcRex+pcRexM8
F: pgtat+pcRex+pcRexM13
G: pgtat+pcRex+pcRexM14
H: pgtat+pcRex+pcRexM17
I: pgtat+pcRex+pcRex13Δ15

Figure 2D:
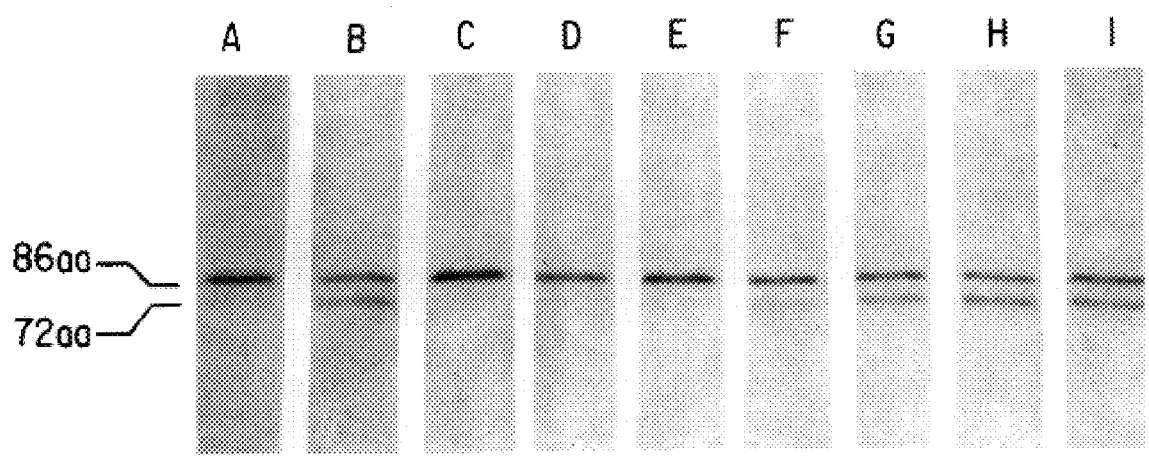

FIG. 2D: As for FIG. 2B (shows that some of the Rex mutants are transdominant over wildtype Rev, namely pcRexM2, pcRexM7, pcRexM8 and pcRexM13 partially):
A: pgtat+pXF3+pXF3
B: pgtat+pcRev+pXF3
C: pgtat+pcRev+pcRexM2
D: pgtat+pcRev+pcRexM7
E: pgtat+pcRev+pcRexM8
F: pgtat+pcRev+pcRexM13
G: pgtat+pcRev+pcRexM14
H: pgtat+pcRev+pcRexM17
I: pgtat+pcRev+pcRex13Δ15

FIG. 3: Rex mutants which have been constructed

FIG. 4: Sequence of the 29 oligonucleotides synthesized to mutagenize the rex coding sequence.

4.2. For 5.2. and 6.2.

Figure 5:
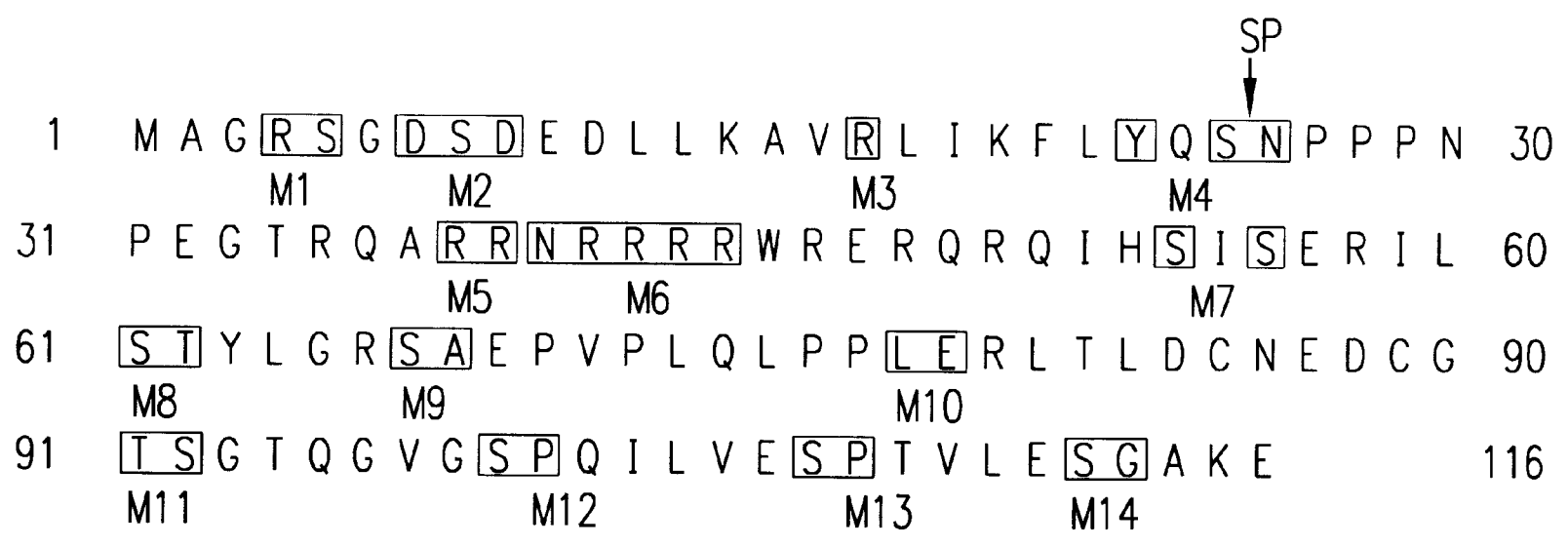

FIG. 5: Location of mutations introduced into the HIV-1 rev gene. The HIV-1 rev gene encodes a 116 amino acid protein with the predicted sequence shown. The border between the two coding exons of rev is indicated (SP). Clustered point (pM) mutations were introduced by oligonucleotide-directed mutagenesis, as indicated by the boxed residues. These mutations were named according to their location within Rev, with pM1 the most N-terminal and pM14 the most C-terminal. All introduced mutations affected from two to four adjacent amino acids and all (except pM7) introduced a unique BglII site into the rev gene sequence. These introduced sites facilitated the subsequent construction of N- and C-terminal deletion (pΔ) mutants. The pΔ mutants are named for the extent of the deletion, e.g. pΔ11/14 is deleted between the introduced pM11 and pM14 mutations.

FIG. 5A: Location of further missense and deletion mutations introduced into the HIV-1 rev gene (−=deleted amino acid).

FIG. 6: DNA and corresponding amino acid sequence of pcREV.

FIG. 7: DNA sequence corresponding to mutation sites M1–M14.

FIG. 8: Immunoprecipitation of the HIV-1 rev and tat trans-activators.

Figure 9:
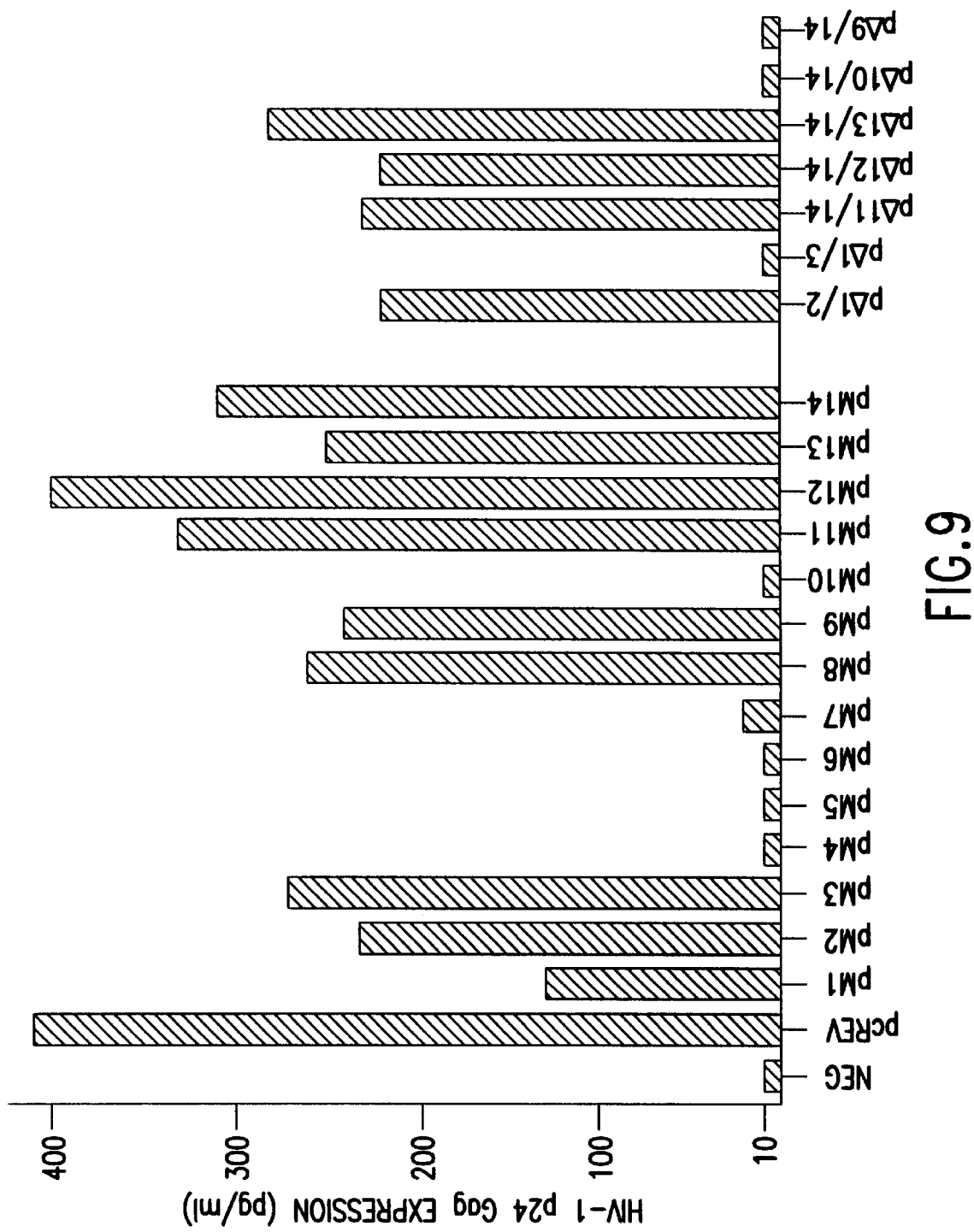

FIG. 9: HIV-1 proviral rescue assay.

FIGS. 10A–J: Subcellular localization of Rev and selected Rev mutants by indirect immunofluorescence.

Figure 11A:
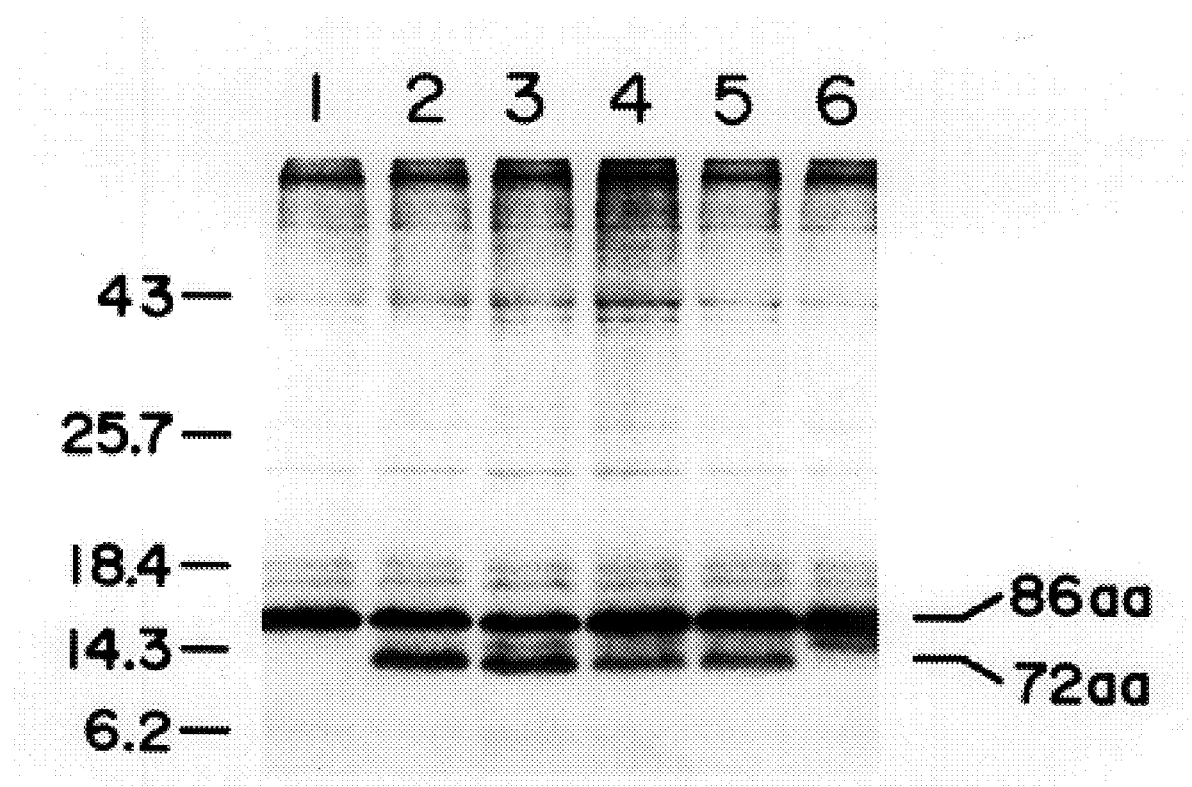
Figure 11B:
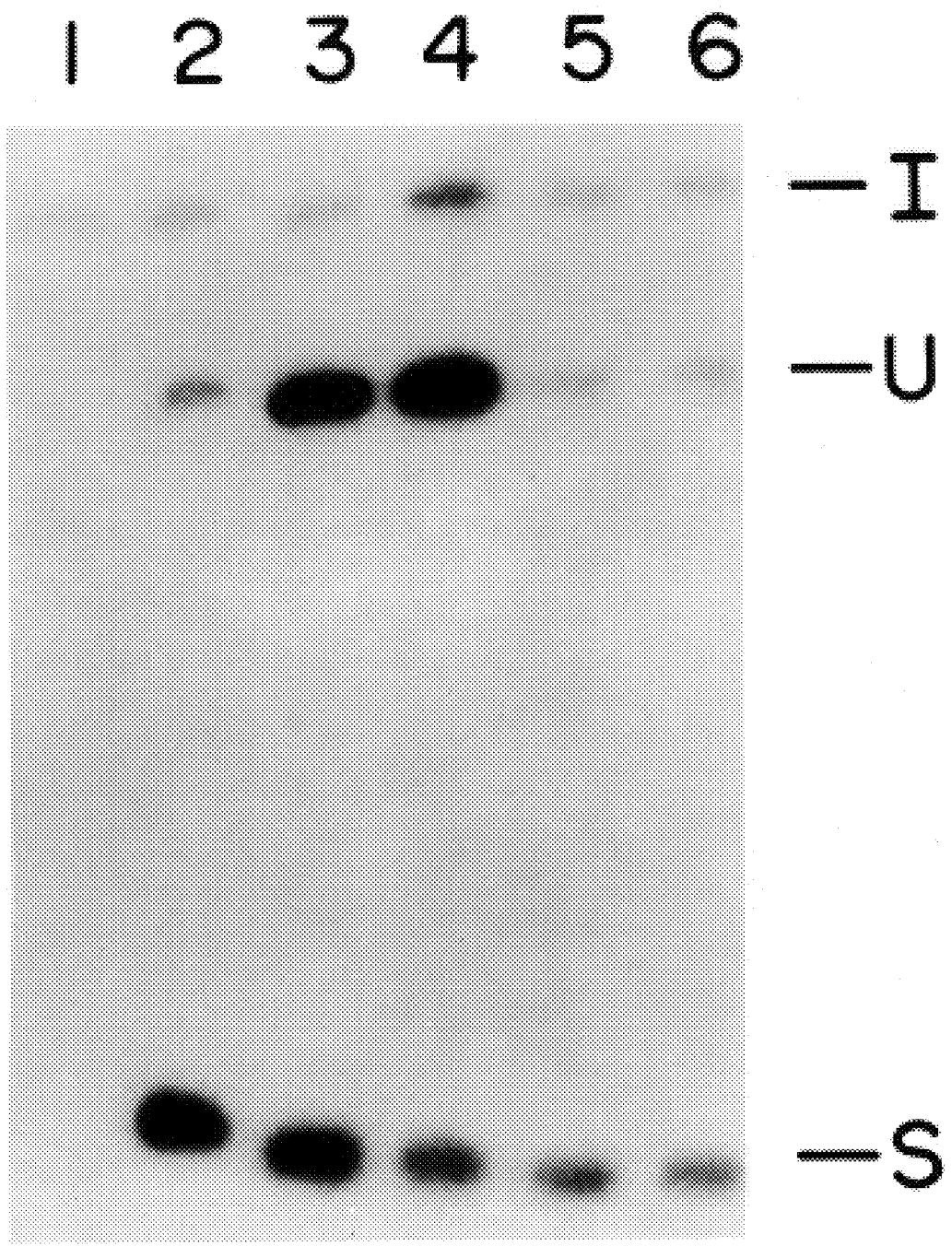

FIGS. 11A and 11B: Analysis of Rev mutants for a dominant negative phenotype.

Figure 12:
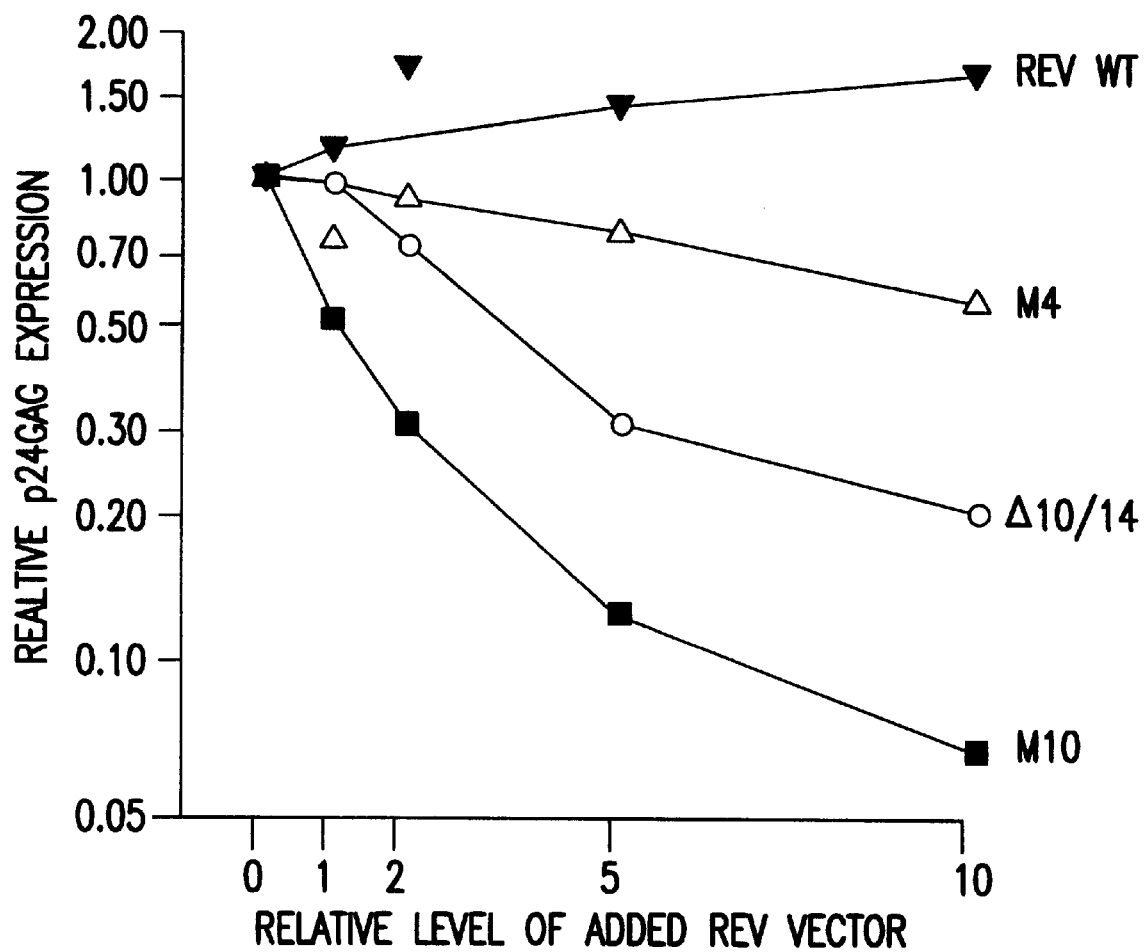

FIG. 12: Competitive inhibition of Rev function.

Figure 12A:
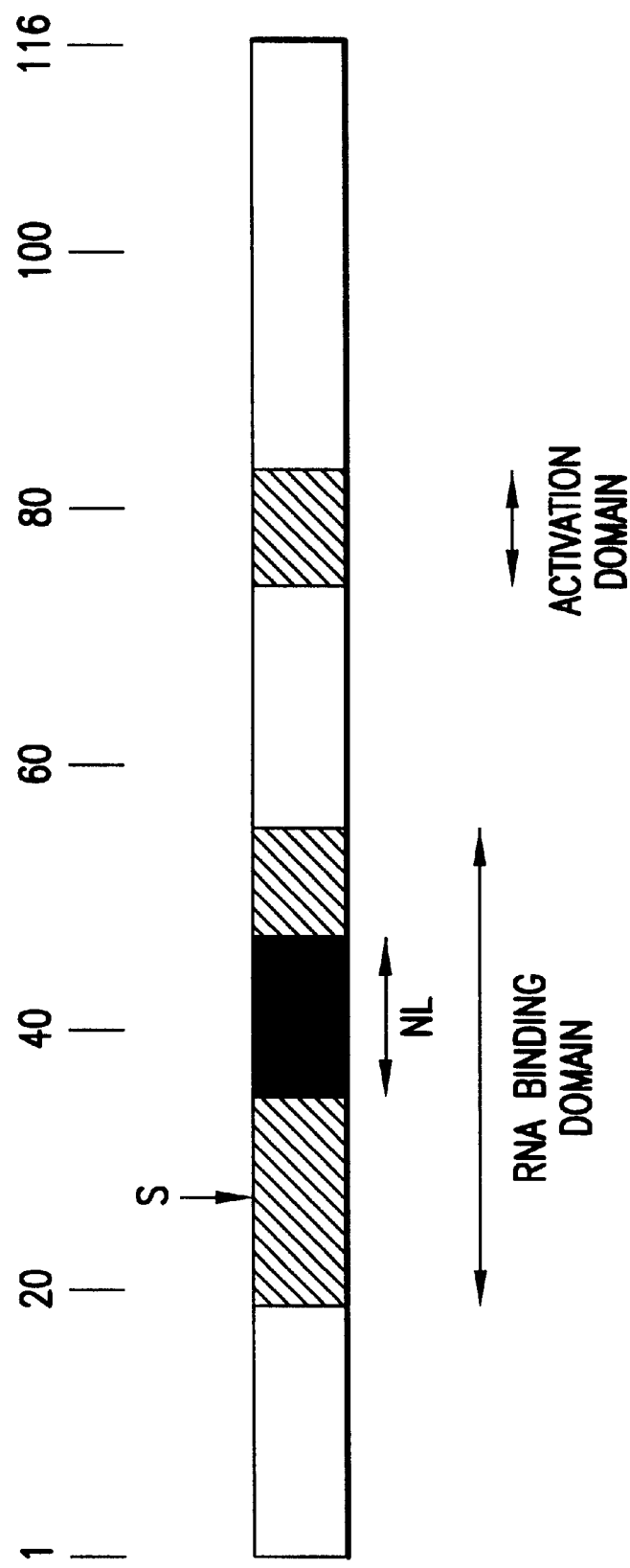

FIG. 12A: Domain structure of the HIV-1 rev trans-activator. The 116 amino acid full-length protein is encoded by two exons separated by an intron largely corresponding to the viral env gene. The "binding" and "activation" domains are shown as hatched boxes encompassing residues 23–56 (approx.) and 78–83, respectively. S=splice junction; NL=highly basic region important for nuclear localization that shares considerable identity with the "Arg-rich" RNA binding motif.

4.3. For 5.3. and 6.3.

Figure 13B:
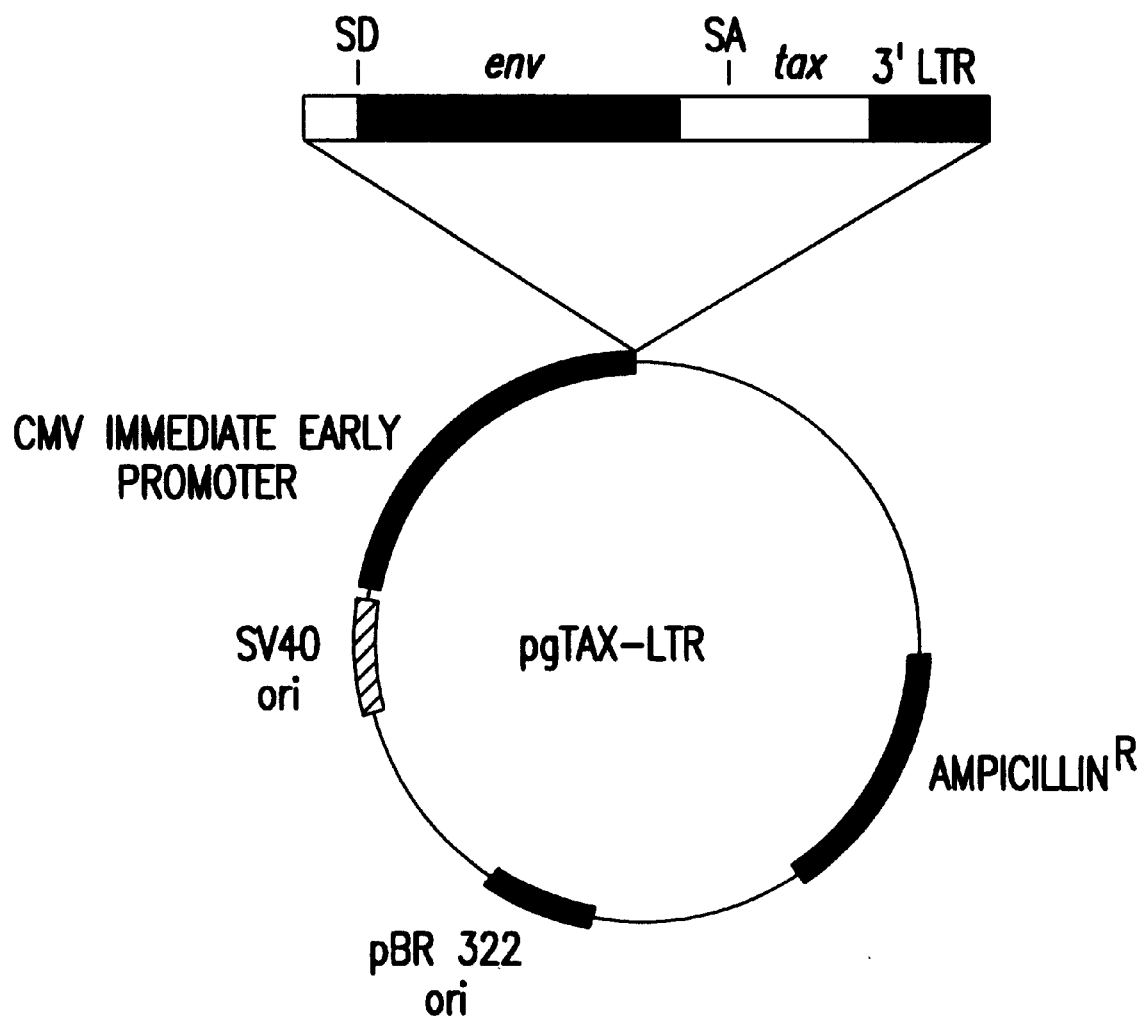

FIGS. 13A and 13B:

(A) Amino acid sequence of the HTLV-I Rex protein and location of each of the 25 point mutations introduced. Nucleotides encoding each of the boxed amino acids were removed and replaced in-frame by an oligonucleotide encoding the aspartic acid-leucine dipeptide.

(B) Structure of the Rex-responsive pgTAX-LTR expression vector. The 3' end of the CR-1 HTLV-I provirus from the HindIII site at map position 5013 (M. Seiki et al., *Proc. Nat. Acad. Sci. USA* 80 [1983] 3618–3622) through the 3' LTR, was inserted into the pBC12/CMV expression vector. This fragment contains the two coding exons for Tax (white boxes), the complete env gene and the entire 3' LTR of HTLV-I including the RexRE (RRX) (S. M. Hanly et al., *Genes Develop.* 3 [1989] 1534–1544).

Figure 14A:
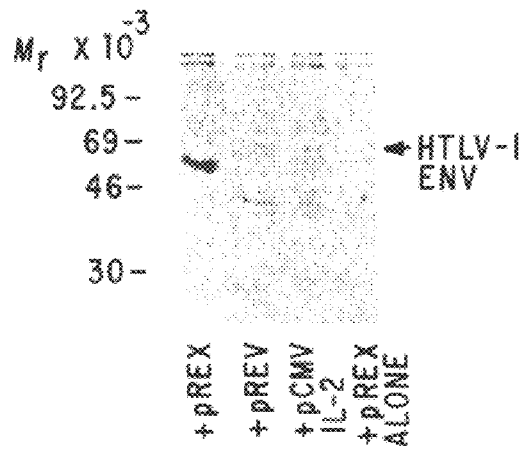
Figure 14B:
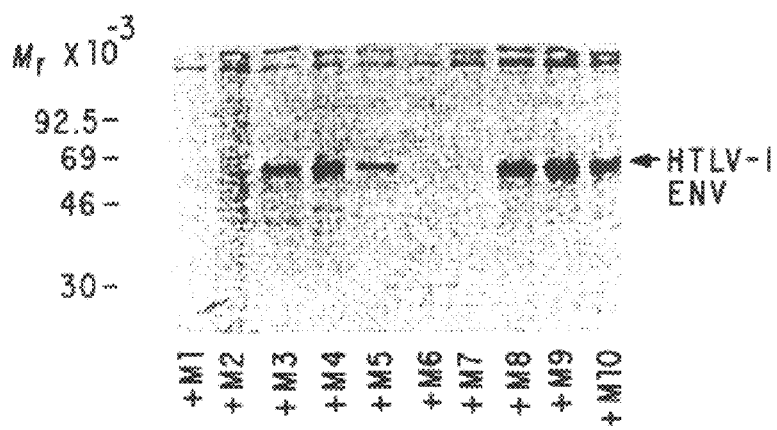

FIGS. 14A and 14B:

(A) Rex, but not Rev or IL-2, activates the expression of HTLV-I Env protein by the pgTAX-LTR vector. Subconfluent cultures of COS cells were cotransfected with pgTAX-LTR and pREX (L. Rimsky et al., *Nature* [1988] 738), pREV (M. H. Malim et al., *Nature* 335 [1988] 181–183) or pCMV-IL-2 (B. R. Cullen, *Cell* 46 [1986] 973–982). In the final lane, cells were transfected with pREX in the absence of pgTAX-LTR. Env protein production was analyzed by immunoprecipitation and gel electrophoresis. The migration of known molecular weight standards is indicated on the left.

(B) Analysis of Rex function of rex mutants. After insertion into the pBC12/CMV expression vector, each of the 25 rex mutants (designated M1–M18 and M21–M27, see FIG. 13A; mutants designated M19 and M20 have not been constructed) was cotransfected with pgTAX-LTR, and the cultures were analyzed for Rex-dependent HTLV-I Env protein expression as described in Example 12.

Figure 15A:
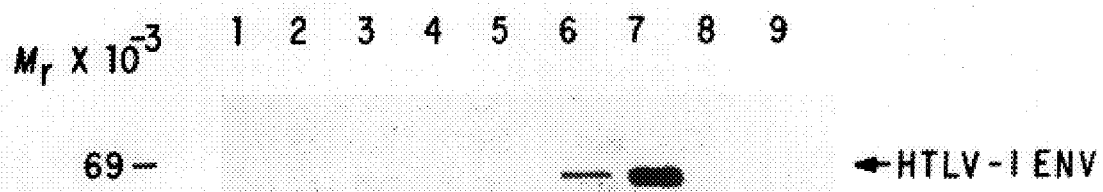
Figure 15B:
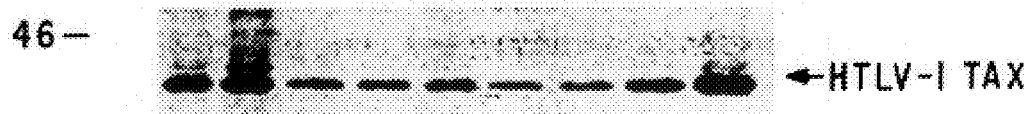
Figure 15C:
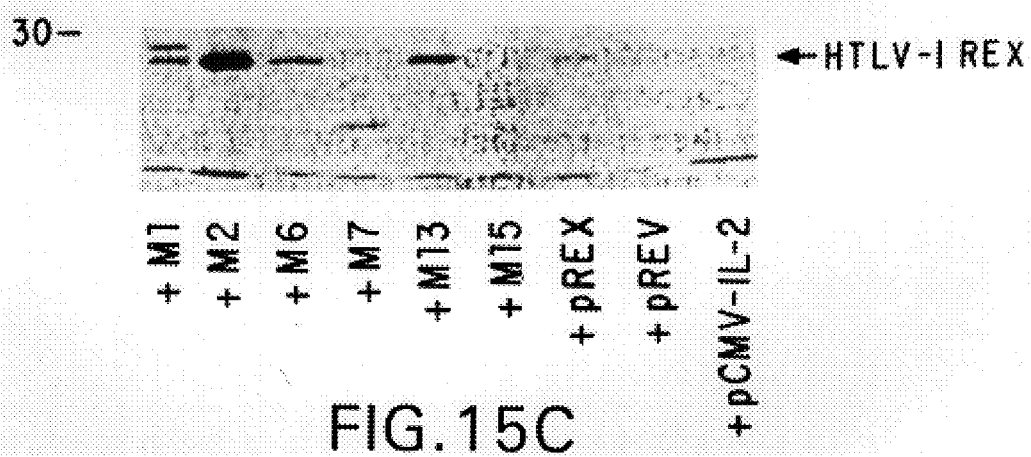

FIGS. 15A–C: Simultaneous analyses by immunoprecipitation of HTLV-I Env, Tax and Rex proteins in COS cells cotransfected with pgTAX-LTR and vectors for the inactive (M1, M2, M6, M7, M13) or impaired (M15) Rex mutants or the wild-type pREX, pREV and pCMV-IL-2 vectors. (A) Env production; (B) Tax production; (C) Wild-type and mutant Rex protein production.

Figure 16:
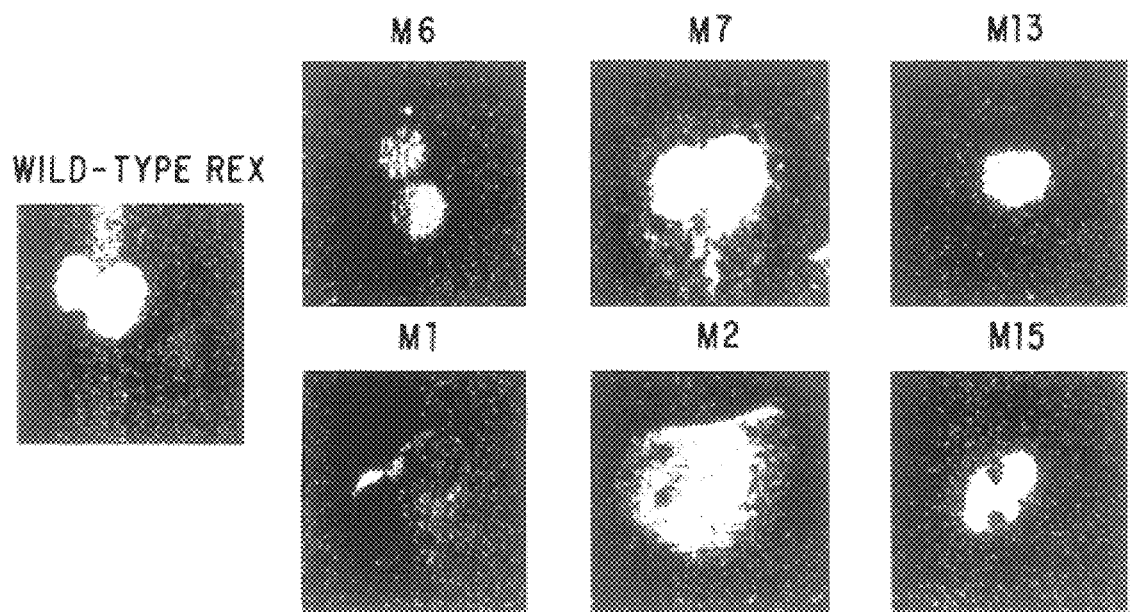

FIG. 16: Subcellular localization of HTLV-I Rex mutants by immunofluorescence. The wild-type, M6, M7 and M13 Rex proteins are localized in the nucleoli and nuclei of expressing cells. In contrast, the M1 Rex protein is detected only in the cytoplasm while the M2 protein is distributed throughout the cell. The M15 mutant is localized in the nuclei of expressing cells but, in contrast to the wild-type Rex protein, appears to be excluded from the nucleoli.

Figure 14C:
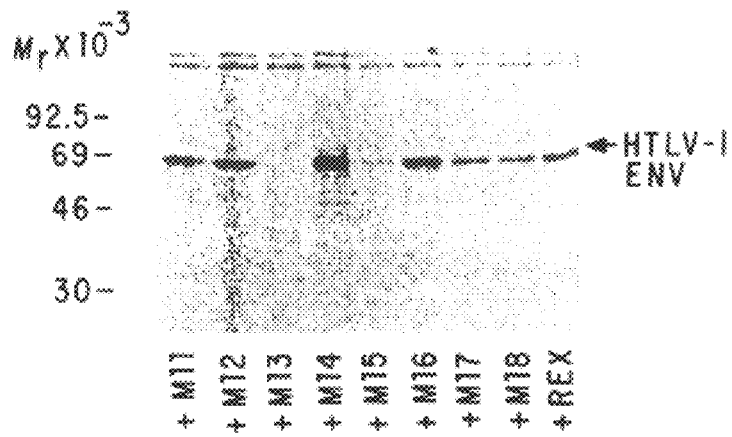

FIGS. 17A–C:

(A) Analysis of the ability of rex mutants to inhibit function of the wild-type Rex protein. Each culture was cotransfected with pgTAX-LTR, pREX and either one Rex mutant (Lanes 1–6), pREX (Lane 7), pREV (Lane 8) or pCMV-IL-2 (Lane 9). HTLV-I Env production was analyzed as in FIG. 14.

(B) The HTLV-I rex transdominant mutants inhibit the function of HIV-I Rev protein. Cells were cotransfected with pgTAT, pREV and pBC/CMV-IL-2 or the M6, M7 and M13 transdominant Rex mutants and assayed for Rev-induced production of the truncated 72 amino acid form of the Tat protein (Lane 2). M6, M7 and M13 (Lanes 3–5) completely inhibited the HIV-1 Rev protein as only the full-length 86 amino acid form of the Tat protein was detected.

(C) The HTLV-I transdominant Rex mutants block Rex rescue of the replication of Rev-deficient HIV-1 provirus. Cells were cotransfected with a rev-deficient HIV-1 proviral plasmid and pREX in the presence of the indicated fold excess of the M1, M6, M7 and M13 mutants. Supernatant levels of HIV-1 p24 Gag protein were measured.

5. DETAILED DESCRIPTION

The procedures and techniques to be used in employing the present invention are known in the art.

Viral species is herewith to be understood as being a taxonomically distinct species such as HTLV-I, HTLV-II, SIV, HIV-1 and HIV-2. The invention concerns in particular the field of retroviruses, especially human retroviruses.

The genes the expression of which it is a goal of the invention to repress are preferably genes coding for an undesirable property, such as a function resulting in activation of the provirus and maturation into infective particles, e.g., rev of HIV-1 and HIV-2.

rev and Rev as used herein mean HIV-1 rev and HIV-1 Rev, respectively, unless specified otherwise. Thus the equivalent rev and Rev of other viral species, such as HIV-2, are specified as "HIV-2 rev (rev2)" and "HIV-2 Rev (Rev2)", respectively, etc.

Insofar as their preparation is not particularly described herein, the compounds, vectors, cell-lines, etc. used as starting materials or reagents are known and publicly available or may be obtained in conventional manner from known and publicly available materials, or equivalent materials may be prepared in conventional manner from known and publicly available materials. Thus e.g. the Rex gene may be recovered from any isolate of HTLV-I and the Rev gene from any isolate of HIV-I and pgTAX-LTR may be recovered e.g. from HUT102 or MT1. Alternatively, genes may be created by chemical synthesis according to the genetic code to produce a protein having the required amino acid sequence. A transdominant repressor of Rex or Rev function is made by standard recombinant DNA methods or by standard chemical methods for peptide synthesis, or by a combination of these methods, all of which are conventional.

5.1.

The invention in one approach concerns transdominant repressors of the Rex function in HTLV-I, especially transdominant repressors of the Rex function in HTLV-I which are also active on the functionally equivalent but structurally unrelated Rev function in HIV-1.

Specifically, modified rex coding sequences were constructed and expressed and found to possess the above property.

The wild-type rex coding sequence (see FIG. 1) was changed using a purchasable mutagenesis system in accordance with "Oligonucleotide-directed in vitro mutagenesis system Version 2", Amersham, England (1988), Code RPN.1523, hereinafter shortened as "Amersham protocol". The construction of the final expression vectors was carried out in stages entailing in succession:

1) preparation of a bacteriophage M13 vector carrying the rex coding sequence,
2) mutagenesis of the rex coding sequence and
3) recloning of the mutated gene into mammalian expression plasmids.

30 mutants were constructed, including one deletion mutant. The position and nature of the 29 site-directed mutations is indicated in FIG. 3. The corresponding oligonucleotides used for mutagenesis are listed in FIG. 4. They all carry a BglII restriction site.

The rex coding sequence was isolated from plasmid pcRex (=pRex) (L. Rimsky et al., *Nature* 335 [1988] 738). Other sources for the wild-type rex gene are available. Thus the rex gene may be cloned e.g. in analogous manner to that described for the gag, pol, env and tax genes of HTLV-I in B. K. De and A. Srinivasan, *Nucl. Ac. Res.* 17 No. 5 (1989) 2142, out of the whole genome of established HTLV-I-infected cell lines such as HUT102 (TIB 162) and MT2 (J. G. Sodroski et al., *Science* 225 [1984] 381; I. Miyoshi et al., *Nature* 294 [1981] 770; V. Manzari et al., *PNAS* 80 [1983] 1574), using e.g. the polymerase chain reaction.

The tat and rev coding sequences were isolated from plasmids pgTat and pcRev (M. H. Malim et al., *Nature* 335 [1988] 181). They may alternatively be isolated e.g. from a HIV proviral clone such as λHXBZ (Catalog No. 70, AIDS Research and Reference Reagent Program, June 1989, NIH).

The biological activity of the various rex genes obtained was tested in a sensitive assay for the action of the HIV-1 rev and the HTLV-I rex gene products by expression of the different genes in COS cells (Gluzman et al., *Cell* 23 [1981] 175. As well as initiating the synthesis of viral structural proteins, the Rev and the Rex proteins both induce the production of a truncated form of the HIV-1 Tat regulatory protein (M. H. Malim et al., *Nature* 335 [1988] 181–183; L. Rimsky et al., *Nature* 335 [1988] 738–740). Coexpression of a genomic HIV-1 tat gene together with a functional HIV-1 rev or a HTLV-I rex gene leads to the cytoplasmic expression of an unspliced tat mRNA encoding a truncated one-exon form of Tat that is 72 amino acids in length. The absence of a functional Rev or Rex protein will allow the expression of a full length Tat protein of 86 amino acids, corresponding to the two-exon form of Tat. Thus the presence of an active trans-repressor of the rev or rex function leads to reduced or abolished production of the 72 amino acids Tat protein. This difference can readily be visualized upon immunoprecipitation analysis.

As shown in FIG. 2C, 6 out of 30 mutants were found, namely pcRexM2, pcRexM7, pcRexM8, pcRexM14, pcRexM17 and pcRex13Δ15, which had a trans-dominant Rex repressor. The same pattern also was found with pcRev (see FIG. 2D), namely for pcRexM2, pcRexM7, pcRexM8 and partially pcRexM13, indicating that transdominancy is not limited to the HTLV-I gene, and that some of the mutants are transdominant for both genes, namely, in this particular instance, pcRexM2, pcRexM7 and pcRexM8.

While some of the results first obtained indicated that the most successful mutations were located between amino acid position 87 and 94, and it thus appeared that a portion of the rex/rev gene lying between about amino acid position 82 and about position 97 was of particular significance in the engineering of trans-dominant Rex/Rev repressors, further testing has shown that the range for preferred positions of the mutations on the Rex protein is broader, i.e. that they may lie at least as near the N-terminus as amino acid position 22 and at least as far toward the C-terminus as amino acid position 101.

5.2.

In a further approach focussing on the Rev function in HIV-1, transdominant rev repressors have also been found. It is possible that some of these at least also inhibit the Rex function in HTLV-I or HTLV-II, but this has not been tested here.

On the other hand it has been found that some of these at least also inhibit the Rev function in HIV-2 and $SIV_{mac}$.

Extensive mutational analysis further has led to the delineation of at least two distinct functional domains within rev that appear to be essential for trans-activation. These domains are envisioned as comprising a "binding domain" which directs the Rev protein to its appropriate target substrate, and an "activation domain" which permits the functional consequences of the binding event, transcriptional activation, to be displayed.

Consequently, two functional domains within rev have been defined: a binding domain likely to direct the Rev protein to its cellular target, and an activation domain permitting the nuclear export of the incompletely spliced RNAs that encode the structural proteins Gag and Env. Mutation of the activation domain of Rev results in the expression of defective Rev protein which acts as trans-dominant inhibitor of Rev function. Such mutants markedly inhibit HIV-1 replication when expressed in transfected cells in culture and are thus also transdominant, as are the mutants obtained under 5.1.

Detailed information concerning this second approach is also apparent from 6.2. hereunder. The transdominant mutants found thereby are designated as pM10, pΔ9/14 and pΔ10/14 (see Examples 4 to 11) and pM21, pM22, pM27, pM28, pM29 and pM32 (see Examples 11a and 11b), whereby pM10 was found to be effective in inhibiting not only HIV-1 rev gene function but HIV-2 rev and $SIV_{mac}$ rev gene function as well.

Preferred under the above 9 transdominant mutants are pM10, pM21 and pM32, especially pM10.

5.3.

In a yet further approach focussing on the Rex function in HTLV-I similarly to 5.1., transdominant rex repressors have also been found and a method developed that permits detection of Rex activities and is useful for the identification of specific inhibitors of Rex function which do not interfere generally with other viral or host cell functions. This Rex inhibitor detection method utilizes a genetic system comprising a Rex-responsive "reporter" gene that encodes an unspliced form of an mRNA that includes a regulatory element, a RexRE (RRX) for instance. In this system, a protein providing Rex function induces the export of this unspliced mRNA from the cell nucleus to the cytoplasm. In the absence of Rex function, this mRNA is spliced before export to the cytoplasm, as indicated above. Upon contacting cells comprising this genetic system with an agent suspected of being an inhibitor of Rex function, specific inhibition of HTLV-I Rex function by that agent is indicated by a decrease in nuclear export of the unspliced form of this particular mRNA, together with no decrease in nuclear export of the spliced form of this same mRNA. This method is useful for detecting, for example, chemical inhibitors of the HTLV-I Rex protein, e.g. inhibitors able to mimic the transdominant domain in a mutant Rex or Rev protein, e.g. low molecular weight chemical inhibitors, as well as transdominant mutant forms of Rex that act as repressors of Rex.

To identify transdominant negative mutations of the rex gene, again a series of point mutations were produced that altered segments of two or three amino acids at various sites throughout the linear sequence of the Rex protein, and several transdominant repressors of HTLV-I Rex protein function identified among these mutants, several of which additionally transdominantly repressed the HTLV-II Rex and/or the HIV-1 Rev protein function and are thus, analogously to some of the mutants found under 5.1., also repressing the phenotypic expression of functionally equivalent genes of more than one viral species.

Accordingly, the invention also relates to a method for identifying a specific inhibitor of the gene activation function of the Rex protein, comprising the several steps defined under 3. above. As noted above the HTLV-I Rex protein is able to replace the function of the HIV-1 Rev protein. In addition it has now been found that Rex also can substitute for the analogous HTLV-II regulatory protein. Thus mRNAs from at least any of these three viruses, which have a response element that is recognized by Rex and at least one appropriate unused splice site, can be used in this method.

Preferably the mRNA comprising the response element and the splice site is encoded by a plasmid comprising the 3' end of an HTLV-I provirus including the coding regions for the Rex and Tax proteins, the complete env gene, the Rex response element RexRE (RRX) and the entire 3' LTR. An example of such a plasmid is pgTAX-LTR. For convenience in mutant analyses that require controlling the ratio of copies of a mutant rex gene to wild-type rex gene copies, the rex gene on pgTAX-LTR is inactivated by a recessive negative mutation and in this system, the active rex gene is provided on the separate plasmid designated pREX. However, for testing chemicals, for instance, the active rex gene could be provided on the same plasmid or other vector DNA as the required mRNA of this system. Further, this active rex gene might comprise a natural sequence variant isolated from a strain of HTLV-I other than that used in the present invention, or any other mutant form of rex gene that is capable of being expressed to produce a protein product which provides the gene activation function of the Rex protein, including induction of export of the above mRNA from the nucleus.

The elements of the genetic system listed above could also be provided by using a DNA segment encoding the entire functional genome of a retrovirus as a part of this genetic system; it can be applied to infected cells. However, for safety reasons as well as convenience, this genetic system preferably is unable to produce any infectious virus. This is accomplished by design into the system of a genetic defect that prevents expression of at least one viral activity which is essential for production of any infectious virus from which some genetic element is used. For example, this may be done by omitting from the system at least a part of one viral gene or by some other mutation.

Preferably the host cell transformed by the rex gene and by the DNA segment encoding the mRNA is exemplified by COS cells which have been transfected by the plasmid vectors described above. Thus the term "transformation" as used herein encompasses the term "transfection" and indicates a genetic transformation involving a vector DNA that encodes an infectious agent, particularly a virus. After transfection such a vector can then spread from the minority of transformed cells in the culture to the majority of other cells by means of infectious virus particles, thereby providing a larger sample of host cells expressing the genes of interest. In addition the transformation of the host cells in the present genetic system need not result in stable constructs; either stable or transient gene expression systems may be used to provide the required mRNA and rex gene. Thus a wide variety of known expression systems may be employed in identifying inhibitors according to the present method.

In this method a decrease in the export of the mRNA that comprises the unused splice site together with no decrease in the export of the spliced form of this mRNA indicates that the agent is a specific inhibitor of an activity of the HTLV-I rex gene or of an activity of a product of the rex gene. For the case of a chemical agent that is found to be a specific inhibitor by use of the present method, the mode of action, in principle, could include specific inhibition of transcription or translation of the mRNA. More likely modes of action, however, include specific inhibition of one or more activities of the Rex protein, including nucleolar localization, recognition of the Rex response element, or the Rex effector function.

Advantageously, the decrease in the nuclear export of the mRNA that comprises the unused splice site is detected by determining the level of production of a first protein, this first protein being encoded by the mRNA that comprises the unused splice site (i.e., only the unspliced form of the mRNA encodes this first protein); and the increase in the nuclear export of the spliced form of the mRNA is detected by determining the level of production of a second protein, this second protein being encoded by the spliced form of this mRNA.

Preferably the mRNA, in the unspliced form, encodes the HTLV-I Env protein. Splicing of this mRNA results in a shorter mRNA that encodes another HTLV-I protein, Tax. In e.g. Examples 12 and 13 below, the nuclear export of the unspliced mRNA having an RexRE (RRX) element is detected by expression of the Env protein. Further, inhibition of such export of the unspliced mRNA, which results from inhibition of Rex function, is detected by a decrease in production of the Env protein. However, since this decrease might also result from some general toxicity of an agent to the virus or the host cell, specific inhibition of rex gene function is indicated by a decrease in Env expression together with no decrease in export of the spliced form of the mRNA, as reflected in no decrease in production of the HTLV-I Tax protein. Thus preferably simultaneous analysis of HTLV-I Env, Tax and Rex protein expression is effected.

In e.g. Examples 12 and 13 below the expression of the Env and Tax proteins is determined by immunoprecipitation with appropriate antibodies and electrophoretic analysis of the resulting precipitates. Alternatives for, e.g., large scale screening of samples for specific inhibition of Rex function include for instance enzyme-linked immunoassay (ELISA) methods for Env and Tax, or alteration of the mRNA by genetic engineering to provide some other, more convenient products for indicating expression of the spliced and nonspliced forms. For example, the mRNA could be altered to encode an enzyme that can be detected by addition of a colorless substrate which produces a color upon hydrolysis, such as $E.$ $coli$ $\beta$-galactosidase. If the gene for this enzyme is inserted in place of the env gene, the unspliced mRNA form would produce this enzyme while the spliced form would not. A second similarly convenient indicator gene could also be encoded in the mRNA so that it would be expressed in the spliced mRNA form, for example, by fusion to the Tax sequences. Further variations on the above approaches for rapid and efficient mass screening would be readily apparent to the man of the art.

In another aspect the invention relates to a reagent kit for screening agents to identify a specific inhibitor of the gene activation function of the Rex protein according to the method above, comprising the components listed under 3. above. This kit optionally further comprises any of the following: media that are used in the culturing of cells; reagents that are used in determining the level of nuclear export of either the spliced or the unspliced form of the reporter mRNA, either directly by nucleic acid hybridization, for example, or indirectly by immunological detection, for instance, of the protein products of the spliced and unspliced forms of this mRNA; and instructions for use of any of the above components of this kit for practising the method of the invention.

The above method has been used for screening various rex gene mutants for dominant negative mutations. When these rex gene mutants were coexpressed with the plasmid pgTAX-LTR in the Rex inhibitor detection system of the invention, a class of mutations was found, similarly as under 5.1., comprising amino acid substitutions in the Rex protein at position 59–60, 64–65 and 119–121, which resulted in proteins that not only lacked Rex function but also acted as transdominant repressors of the function of the wild-type Rex protein and which also acted as transdominant repressors of the function of the wild-type Rev protein.

This mutational analysis also produced a second class of negative mutants comprising substitutions at Rex amino acid positions 5–7 and 14–15 which lacked Rex function. These mutant proteins were neither appropriately targeted to the cell nucleus nor transdominant. Further, a third class of negative mutants, exemplified by a single mutant which has substitutions at Rex amino acid positions 141–143, retains partial Rex function and was targeted to the nucleus but failed to localize in the nucleolar region of the nucleus; this mutant protein was also not a transdominant repressor of HTLV-I Rex function. These results raise the possibility that the nucleolar localization activity may involve sequences other than the positively charged residues identified at the amino terminus (H. Siomi et al. *Cell* 55 [1988] 197–209). In addition, the findings suggest that for a Rex protein mutant to serve as a transdominant repressor of Rex function, that mutant may need to have not only a nuclear targeting activity but also a distinct nucleolar localization activity of the Rex protein.

These findings on the Rex mutants here also define approximate bounds of at least two functionally distinct peptide domains within the Rex protein, a first one involved in nuclear and nucleolar targeting and a second involved in effector activity. The Rex mutants deficient in nuclear targeting are located in the positively charged peptide domain at the amino terminus of Rex that has been previously shown to function as a nucleolar localization signal; when a peptide comprising the amino terminal twenty amino aceds was attached to another protein by recombinant DNA means, this domain induced both nuclear targeting and nucleolar localization of that protein in a pattern similar to that observed for Rex (H. Siomi et al. [1988] supra). Thus it is not likely that the mutant at Rex amino acid positions 141–143 lies in a region that is required for nucleolar localization, even though this mutant was targeted to the nucleus but failed to localize in the nucleolar region of the nucleus. Rather, the alteration in this mutant most likely affects the Rex nucleolar localization function in the amino terminal domain indirectly, for instance, through interference with proper protein folding.

The second major functionally distinct domain of Rex encompasses amino acids 59–60 (tyrosine-isoleucine), 64–65 (tyrosine-tryptophan) and 119–121 (threonine-phenylalanine-histidine). An alteration at each of these discrete sites (M6, M7 and M13 mutants) leads to the production of a Rex protein that both lacks biological activity and displays transdominant inhibitory properties. Five different mutations having no effect on Rex function separate the region of M6 and M7 from that of M13 in the linear sequence of the Rex protein, indicating that the interaction of these two discrete regions within this functional domain may require proper protein folding. Thus the entire linear portion of the Rex protein encompassing these two regions of amino acids that are most critical for Rex effector function appears to contribute to the effector function of the Rex protein and, therefore, represents the domain to be mutated to produce transdominant repressors of Rex.

The present findings do not address the domain of Rex in which is located the activity required for recognition of the RexRE (RRX) in an mRNA. Accordingly, it is not known whether to serve as a transdominant repressor of Rex function a mutant rex protein must retain the ability to bind (directly or indirectly) to the RexRE, or to the recognition element of some other virus that is recognized by Rex.

Another aspect of the invention relates to a DNA segment that encodes a transdominant repressor of the function of the HTLV-I Rex protein, as well as such a transdominant repressor. This repressor is a protein that is modified from a wild-type form of the Rex protein by at least one mutation that negatively affects the effector activity of the Rex protein. This represssor also has substantially the nucleolar localization activity of the wild-type form of the Rex protein. In particular, the negative mutation of this repressor is one that affects an amino acid in the peptide domain of the wild-type Rex protein that comprises from about amino acid position 59 to about amino acid position 121, more particularly in any of the following positions: 59, 60, 64, 65, 119, 120 and 121. The DNA segment encoding the Rex repressor is exemplified by any of the following mutant rex genes: M6, M7, M13 and variants and derivatives thereof which exhibit transdominant repression of HTLV-I Rev protein function.

The sequence of this DNA segment is derived from the Rex gene of any isolate of HTLV-I (L. Rimsky et al., *Nature* 335 [1988] 738–740; Goh et al., *Science* 227 [1985] 1227–1228) or is created by chemical synthesis. The transdominant repressor of Rex function is made by standard recombinant DNA methods or by standard chemical methods for peptide synthesis or by a combination of these methods, all of which are well-known in the art of genetic engineering.

The mutations that negatively affect the effector activity of the Rex protein are exemplified as described herein. However other types of mutations designed to produce localized effects on the protein structure at or close to these same amino acid positions also are highly likely to produce variants and derivatives of Rex which exhibit transdominant repression of HTLV-I Rex protein function according to the present invention. Such localized defects include, for example, deletions or insertions of single amino acids or substitutions of chemically or structurally similar amino acids. On the other hand, more extensive deletions or insertions, or substitutions that disrupt secondary structure (e.g., a proline in a β-sheet region) are highly likely to have effects on distant parts of the protein through influence on protein folding; therefore, such mutations at the indicated positions within the domain required for Rex effector function are not likely to produce mutant Rex proteins that retain substantially the nucleolar localization activity of the wild-type form of the Rex protein.

The transdominant Rex mutants of 5.3. above were also tested for inhibition of Rev function and found to be repressors of HIV-1 Rev as well. The anti-viral potential of this class of transdominant Rex mutants has been demonstrated using an assay for inhibition of HIV-1 replication.

In addition and as already mentioned above it has now been discovered that HTLV-I Rex can also functionally substitute for the analogous HTLV-II regulatory protein, even though the nucleotide sequence of the corresponding response element in HTLV-II has a somewhat different stem and loop structure from that of the RexRE (RRX) in HTLV-I.

The invention thus further relates to a method of inhibiting replication of HIV-1, HTLV-I and HTLV-II comprising introducing a DNA segment as defined above which encodes a transdominant repressor of Rex function into a cell having the ability to replicate one of these viruses. This cell also has the ability to express the DNA segment to produce the transdominant repressor. This cell may be one that was previously infected by one or more of these viruses or this cell may be an uninfected target cell for one or more of these viruses.

For the preferred embodiment of the genetic system mentioned above, a Rex responsive reporter plasmid, pgTAX-LTR, was prepared (FIG. 13B). Briefly, the pgTAX-LTR vector contains the two protein coding exons of the tax gene separated by the HTLV-I env gene and a complete HTLV-I 3' LTR containing the RexRE (RRE). Expression of these HTLV-I sequences is promoted by the immediate early region of the human cytomegalovirus and additional polyadenylation sequences are provided by the 3' region of the rat preproinsulin gene (B. R. Cullen, Cell 46 [1986] 973–982). This vector produces Env only in the presence of Rex, however Tax is synthesized in the presence or absence of Rex. This vector does not itself produce Rex due to the introduction of a mutation at the SphI site which is coincident with the Rex translation initiation codon. In the absence of Rex, pgTAX-LTR produces Tax protein reflecting translation of the spliced mRNA species from this vector that lacks virtually all of the env sequences. However, when pgTAX-LTR is cotransfected with the rex expression plasmid pREX, synthesis of the HTLV-I Env protein is activated. This 62–68 kD protein is readily identified as evidenced by immunoprecipitation with the anti-HTLV-I envelope monoclonal antibody 0.5 alpha (S. Matsushita et al., Proc. Natl. Acad. Sci. USA 83 [1986] 2672–2676) (FIG. 14A, Lane 1). In contrast, no HTLV-I Env protein is detected when pREX is replaced by either pREV (Lane 2) or pCMV-IL-2 (Lane 3), which encode respectively the HIV-1 Rev protein and human IL-2 polypeptide. Similarly, no Env protein is identified when cells are transfected with pREX in the absence of pgTAX-LTR (Lane 4).

Thus in the genetic system defined above HTLV-I Env expression by pgTAX-LTR is specifically induced in the presence of a protein having the gene activation function of the wild-type Rex protein. In the system including a gene that provides a protein having Rex function, if contact with an agent inhibits Rex function, Tax protein continues to be produced unless that agent affects some viral or cellular activity that is not related to the expression of the gene or the product of the gene that provides Rex function, i.e. unless the agent is not a specific inhibitor of that gene or its product. Thus, as indicated in Example 12 and FIG. 15, advantageously the exemplary method for identifying specific inhibitors of Rex function includes the simultaneous analysis of HTLV-I Env, Tax and Rex protein expression.

It may be noted that in the case of specific inhibition of Rex function by transdominant repressors described below and in FIG. 15 the production of HTLV-I Tax protein evidently increases. This is probably a result of an increase in the nuclear export of the spliced form of the Env mRNA that is not exported prior to splicing due to a lack of Rex function. However, in principle a specific inhibitor of Rex function may prevent splicing of the mRNA but not induce export of the unspliced RNA. Accordingly, the present method for identifying specific inhibitors of Rex function requires only that there be no decrease in the nuclear export of the spliced mRNA that, in the present situation, produces the Tax protein.

The use of this system is exemplified in Example 12 below. In this mutational analysis again oligonucleotide-directed mutagenesis, in the M13 bacteriophage, was employed to alter the primary sequence of the rex gene, at 25 discrete sites (FIG. 13A). The boxed amino acids were replaced by the dipeptide aspartic acid-leucine by insertion of an in-frame oligonucleotide duplex which also contained the diagnostic BglII restriction site. Each of these rex mutants was then inserted into the pBC12/CMV eucaryotic expression vector (B. R. Cullen, Cell 46 [1986] 973–982) and the mutations were verified by DNA sequencing.

Each of the rex mutations was examined for biological activity by cotransfection with the pgTAX-LTR vector. While nineteen of these rex mutants displayed a wild-type phenotype, five mutants (M1, M2, M6, M7 and M13) lacked apparent env gene activation activity and one mutant (M15) displayed only partial function (FIG. 14B). COS cells were next cotransfected with these six rex defective mutants and the pgTAX-LTR vector, followed by simultaneous analysis of HTLV-I Env, Tax and Rex protein expression as described in Example 12 (see also FIG. 15 A–C). While HTLV-I Env was only detected in the presence of the wild-type Rex protein (FIG. 15A, Lane 7) or the partially active M15 mutant (FIG. 15A, Lane 6), the 40 kD Tax protein was detected in all of the cultures (FIG. 15B). Thus the lack of env gene expression observed with the M1, M2, M6, M7 and M13 mutants is due to the specific loss of Rex biological activity rather than non-specific, toxic effects of these proteins in the transfected COS cultures. Each of the mutant Rex proteins was also identified in these cultures indicating that all of the mutants were expressed in a stable manner (FIG. 15C). The M2, M6 and M13 mutants migrated in a manner that was indistinguishable from the wild-type Rex protein (FIG. 15C, Lanes 2, 3, 5 and 7), whereas the M7 and M15 proteins exhibited a smaller apparent molecular weight (Lanes 4 and 6) and the M1 mutant yielded an electrophoretic doublet of proteins (Lane 1). Sequencing of the protein coding regions in the M1, M7 and M15 mutants failed to reveal any changes other than the specific mutations introduced. Thus the biochemical basis for these apparent differences in size likely reflects altered post-translational processing of these mutant Rex proteins.

Like the wild-type Rex protein, in situ immunofluorescent staining of cells transfected with the biologically inactive M6, M7 or M13 Rex mutants, as detailed in Example 12, revealed normal targeting to the nucleoli and nuclei of expressing cells (FIG. 16). In sharp contrast the M1 mutant protein was detectable only in the cytoplasmic compartment, while the M2 Rex mutant was distributed in an approximately homogeneous manner throughout the cell. Consistent with these findings is the fact that the M1 and M2 mutations altered basic amino acid residues located within the positively charged peptide domain that functions as a nucleolar localization signal. The partially active M15 mutation lead to a pattern of nuclear localization of mutant Rex protein, but unlike the wild-type Rex protein the M15 protein did not localize further within the nucleolar region of the nucleus and, in fact, M15 appeared to be excluded from the nucleoli (FIG. 16). These results suggest that residues away from the basic amino acids at the N-terminus may be involved in or contribute to the nucleolar localization of Rex.

Figure 17A:
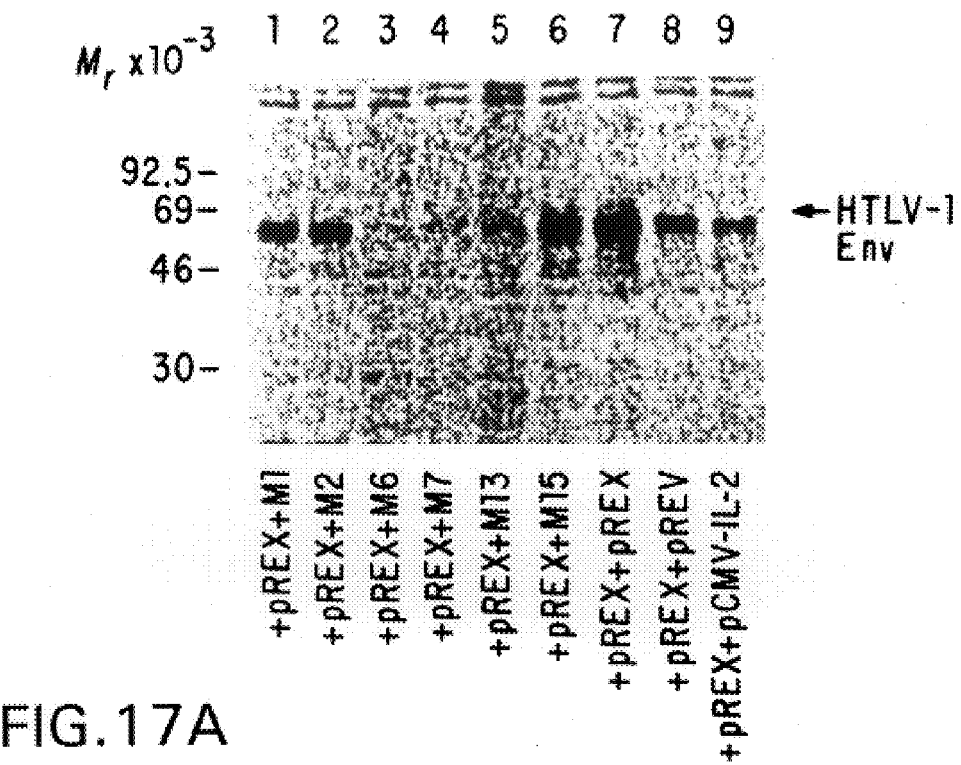

The rex mutants were also examined for their capacity to block the biological action of the wild-type HTLV-I Rex protein and the wild-type HIV-1 Rev protein (FIG. 17). When cotransfected with pgTAX-LTR and pREX in COS cells (Panel A), a 10 fold molar excess of the M6, M7 and M13 mutants displayed a dominant negative phenotype in that the action of the wild-type Rex protein was markedly inhibited (Lanes 3–5). In contrast, the M1, M2 and M15 proteins acted as recessive negative mutants since the action of the wild-type protein was not altered (Lanes 1, 2, 6). Similarly, the Rev protein of HIV-1 did not interfere with the action of the Rex protein (Lane 8) nor did IL-2 (Lane 9).

Figure 17B:
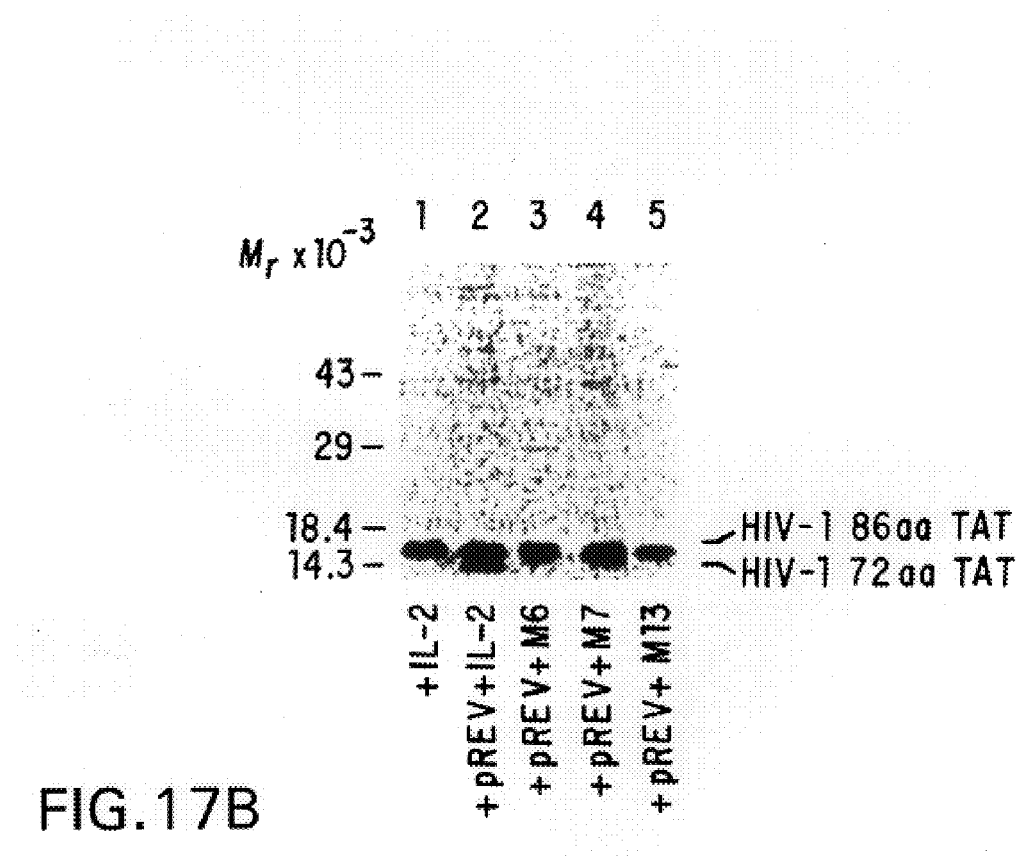
Figure 17C:
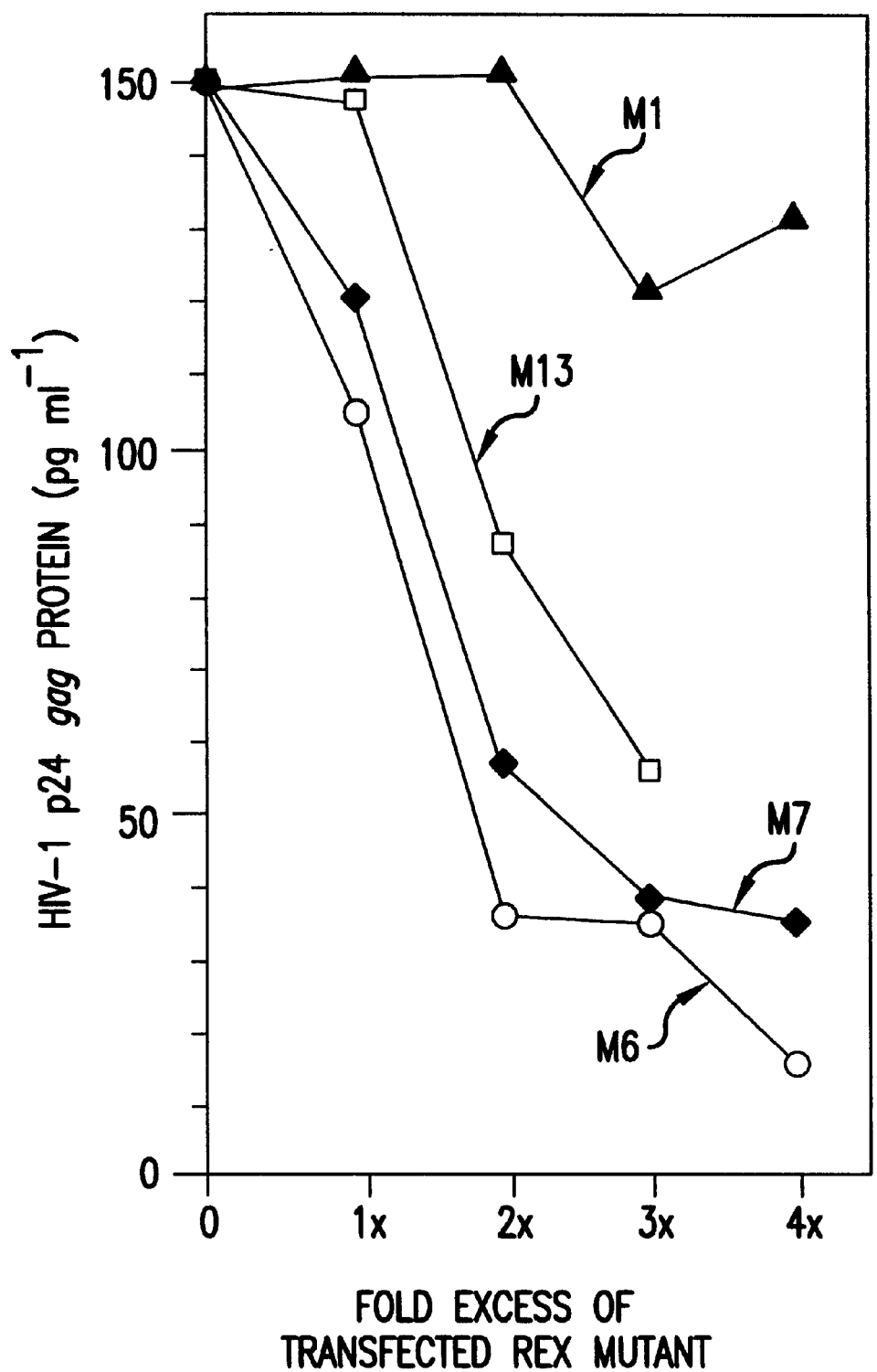

The capacity of the trans-dominant Rex mutants to block the function of Rev in the HIV-1 system was examined next (FIG. 17B). When cotransfected with pgTAT and pREV in COS cells, a 10-fold molar excess of M6, M7 or M13 Rex mutants inhibited the action of the Rev protein (Lanes 3, 4, 5) as evidenced by diminished expression of the 72 amino acid form of the Tat protein. The ability of these transdominant Rex mutants to block HIV-1 viral replication was also studied (FIG. 17C). Replication of a Rev-deficient HIV-1 provirus, pHXB2-Bam-p3 (L. Rimsky et al., Nature 335 [1988] 738) in the presence of Rex and graded amounts of transdominant Rex mutants was studied by transfection of COS cells with these plasmids. As indicated by synthesized levels of the HIV-1 p24 Gag protein in culture supernatants, the transdominant Rex mutants (M6, M7 and M13) produced dose-related inhibition of HIV-1 replication. In contrast, the recessive negative M1 mutant of Rex was without significant effect on HIV-1 replication.

Together, these findings with the various rex mutants of Examples 12 and 13 hereunder indicate the approximate boundaries within the Rex protein of at least two different structural domains having different activities. Thus one domain is defined by the M1 and M2 mutations, is located at the N-terminus, involves amino acids 5–7 and 14–15 and appears to play a role in targeting of the protein to the nucleus and thence to the nucleolus. This positively charged domain may also be involved in Rex binding either directly to the RexRE (RRX) or to other proteins that directly contact this RNA element. The second domain, which has been described above, is critical for the Rex effector function and, therefore, can be mutated to produce transdominant repressors.

5.4

Summarizing the findings under 5.1., 5.2. and 5.3. above, it is concluded that:
a) a generally applicable principle has been found for producing viral inhibitors by mutating a critical regulatory protein, such as Rex or Rev;
b) this principle appears applicable to the production of mutant regulatory proteins acting on a plurality of viral species; and
c) the specific transdominant mutants which have been constructed and identified are:

HTLV-I Rex mutants effective in inhibiting HTLV-I rex gene function:
  pcRexM2, pcRexM7, pcRexM8, pcRexM17 and pcRex13Δ15 (see 5.1. and Examples 1–3);
  M6, M7 and M13 (see 5.3. and Examples 12–13);

HIV-1 Rev mutants effective in inhibiting HIV-1 rev gene function:
  pM10, pΔ9/14 and pΔ10/14 (see 5.2. and Examples 4–11);
  pM21, pM22, pM27, pM28, pM29 and pM32 (see 5.2. and Examples 11a and 11b);

HTLV-I Rex mutants effective in inhibiting HTLV-I rex gene function and also effective in inhibiting HIV-1 rev gene function:
  pcRexM2, pcRexM7 and pcRexM8 (see 5.1. and Example 3);
  M6, M7 and M13 (see 5.3. and Examples 12–13);

HTLV-I Rex mutants effective in inhibiting HTLV-I and HTLV-II rex and HIV-I rev gene function:
  M6, M7 and M13 (see 5.3. and Examples 12–13);

HIV-1 Rev mutant effective in inhibiting HIV-1 rev gene function and also effective in inhibiting HIV-2 rev and $SIV_{mac}$ rev gene function:
  pM10 (see 5.2. and Example 11b).

6. EXAMPLES

The following Examples illustrate the invention. They are not to be viewed as being limitative.

6.1.

Example 1

Construction of a Transdominant HTLV-I Rex Gene
1. Cloning of the Rex Coding Sequence into the RF-DNA of Bacteriophage M13

5 µg pcRex DNA were treated with 10 units each of restriction enzymes HindIII and EcoRI in 20 µl restriction enzyme incubation buffer (10 mM Tris-HCl pH 7.5; 10 mM $MgCl_2$; 50 mM NaCl; 1 mM Dithiothreitol) at 37° C. for 3 hours. The reaction mixture was directly loaded onto a 1.% agarose gel (Seakem FMC Inc., Rockland, Me., USA) containing 1 µg/ml ethidium bromide and subjected to electrophoresis at 50 V; 25 mA for 4 hours in Tris-acetate buffer (T. Maniatis et al., *Molecular Cloning, A Laboratory Manual* [1982], Cold Spring Harbor Laboratory, New York, p. 156). The separated DNA was visualized on a 366 nm UV-lamp and an appropriate gel slice containing the 1.5 kb rex fragment was excised. This gel section was placed in a dialysis bag containing 500 µl Tris-borate buffer (Maniatis, p. 156). The DNA was electroeluted into the buffer and precipitated at −20° C. with ethanol.

5 µg of bacteriophage M13mp10 RF-DNA were treated with the restriction enzymes HindIII and EcoRI and the 7.2 kb vector M13 fragment was isolated from a 1% agarose gel in the same way.

200 ng phage DNA and 1 µg cRex DNA were mixed in 20 µl ligation buffer (50 mM Tris-HCl pH 7.4; 10 mM $MgCl_2$; 10 mM Dithiothreitol; 1 mM ATP) with 1 unit of T4-DNA-ligase and incubated for 15 hours at 16° C. This reaction mixture was used directly to transform and plate out *E. coli* strain TG1 (Amersham protocol, p. 16–18).

The DNA of appropriate phage plaques was checked by endonuclease cleavage with the restriction enzymes HindIII and EcoRI, followed by analytical gel electrophoresis through a 1% agarose gel containing 10 µg/ml ethidium bromide in Tris-acetate buffer. A bacteriophage carrying the rex coding sequence was identified and designated mp10rex.

Single-stranded mp10rex DNA was isolated using a large scale preparation protocol (Amersham protocol p.24–25).

Mutagenesis of the Rex Coding Sequence in mp10rex

As a prerequisite of the mutagenesis it was necessary to synthesize appropriate single-stranded DNA molecules. 29 oligonucleotides (see FIG. 4) were made, which eventually led to 30 mutants, of which the following seven oligonucleotides led directly or (see Example 2) indirectly to the mutants which were found to be successful in terms of transdominant phenotype:

```
(1)
5'-  TG GAC AGA GTC TTA GAT CTG GAT ACC CAG TCT -3'
                      BglII (2)
5'-  AC TAT GTT CGG CCA GAT CTC ATC GTC ACG CCC -3'
                      BglII (3)
5'-  CC TAC ATC GTC ACA GAT CTC TGG CCA CCT GTC -3'
                      BglII (4)
5'-  TCG GCT CAG CTC TTA GAT CTC TTA TCC CTC GA  -3'
                      BglII (5)
5'-  AG CTC TAC AGT TCA GAT CTC CTC GAC TCC CCT -3'
                      BglII (6)
5'-  GT TCC TTA TCC CTA GAT CTC CCT CCT TCC CCA -3'
                      BglII (7)
5'-  CT CCT TCC CCA CCA GAT CTA CCT CTA AGA CCC -3'
                      BglII
```

Oligonucleotide (1) is substituting the amino acid residues phenylalanine (position 30), phenylalanine (position 31)

and serine (position 32) in the Rex protein by the amino acids leucine (position 30), aspartic acid (position 31) and leucine (position 32).

Oligonucleotide (2) is substituting the amino acid residues alanine (position 58) and tyrosine (position 59) in the Rex protein by the amino acids aspartic acid (position 58) and leucine (position 59).

Oligonucleotide (3) is substituting the amino acid residues proline (position 63) and tyrosine (position 64) in the Rex protein by the amino acids aspartic acid (position 63) and leucine (position 64).

Oligonucleotide (4) is substituting the amino acid residues tyrosine (position 87), serine (position 88) and serine (position 89) in the Rex protein by the amino acids leucine (position 87), aspartic acid (position 88) and leucine (position 89).

Oligonucleotide (5) is substituting the amino acid residues leucine (position 90) and serine (position 91) by the amino acids aspartic acid (position 90) and leucine (position 91).

Oligonucleotide (6) is substituting the amino acid residue serine (position 94) by the amino acid leucine.

Oligonucleotide (7) is substituting the amino acid residues arginine (position 100) and glutamic acid (position 101) in the Rex protein by the amino acids aspartic acid (position 100) and leucine (position 101).

All oligonucleotides are introducing BglII restriction sites in frame of the rex coding sequence.

The oligonucleotides have been synthesized on solid support on an Applied Biosystems 380A synthesizer using β-cyano-ethylphosphoamidite chemistry. Purification was done by 8% polyacrylamide gel electrophoresis, followed by elution of the main product and ethanol precipitation. Phosphorylation of the oligonucleotides using ATP and polynucleotide kinase was carried out as described in the Amersham protocol, p. 13. The oligonucleotide-directed mutagenesis reaction was effected according to the Amersham protocol, p. 13–16. This was followed by transformation and plating out of $E.$ $coli$ strain TG1 as described on pages 16–18. The DNA of different plaques was screened by restriction endonuclease analysis using the enzymes BglII and EcoRI.

From all seven mutations one clone was identified carrying the introduced mutation in the rex coding sequence. These clones have been designated mp10rexM2, mp10rexM7, mp10rexM8, mp10rexM13, mp10rexM14, mp10rexM16 and mp10rexM17. A further clone, mp10rexM15, was used in the construction of the deletion mutant (see Example 2).

3. Recloning of the Mutated Rex Genes into Mammalian Expression Plasmids

The mutated rex genes were moved back from the bacteriophage M13 vectors into the original expression plasmid. 5 μg pcRex DNA were incubated with 10 units HindIII and 10 units EcoRI restriction endonuclease at 37° C. for 3 hours. The reaction mixture was loaded directly onto a 1% agarose gel containing 10 μg/ml ethidium bromide and subjected to electrophoresis in Tris-acetate buffer at 50 V; 25 mA for 4 hours. The HindIII-EcoRI vector fragment was electroeluted out of the appropriate gel slice and precipitated with ethanol.

5 μg of the mutants obtained under 2. were treated in the same way and fragments containing the rex coding sequence were isolated.

200 ng of the isolated vector fragment and 1 μg of the isolated rex sequences were mixed together separately in 20 μl of ligation buffer in the presence of 1 unit of T4-DNA-ligase and incubated at 16° C. for 15 hours. The resultant reaction mixtures were directly used to transform $E.$ $coli$ strain HB101. The DNAs of different bacterial colonies were analysed using the restriction endonucleases HindIII, Asp718 and BglII, followed by analytical gel electrophoresis through a 1% agarose gel. Plasmids identified in this way carrying the rex genes were designated pcRexM2, pcRexM7, pcRexM8, pcRexM13, pcRexM14, pcRexM15, pcRexM16 and pcRexM17, respectively.

Example 2

Construction of a Deletion Mutation in the Rex Coding Sequence

5 μg of pcRexM13 DNA were treated with 10 units each of the restriction enzymes BglII and EcoRI. The larger DNA fragment, containing the vector backbone and the 5' portion of the rex coding sequence, was isolated as described above. In parallel 5 μg of pcRexM15 DNA treated in analogous manner and the smaller DNA fragment, containing the 3' portion of the rex coding sequence was isolated.

200 ng of the isolated pcRexM13 DNA fragment were mixed with 1 μg of the isolated pcRexM15 DNA fragment and incubated in 20 μl of ligation buffer in the presence of 1 unit of T4-DNA ligase at 16° C. for 15 hours. This manipulation led to a rex coding sequence where amino acid positions 87, 88 and 89 are identical with those in clone pcRexM13 and position 90–94 are deleted.

The reaction mixture was then directly used to transform $E.$ $coli$ strain HB101. The DNA of different clones was screened by restriction endonuclease digestion employing the enzymes HindIII, Asp718 and BglII. A positive clone was identified and designated pcRex13Δ15.

Example 3

Biological Activity a) Biological Activity of the Mutant Genes in Mammalian Cells 0.25 μg of the rex wild-type and each mutant rex gene expression vector was mixed with 0.25 μg of the genomic tat (trans-activator) expression vector pgtat (M. H. Malim et al., Nature 335 [1988] 181) and transfected into the Cos cell line as described in B. R. Cullen, Meth. Enzymol. 152 (1987) 684–703. At 60 hours post-transfection cultures were labeled for 3 hours with 300 μCi/ml of $^{35}$S-cysteine and analyzed for expression of the HIV-1 Tat and the HTLV-I Rex protein by immunoprecipitation analysis. A rabbit anti-peptide antibody directed against amino acid residues 1–61 of Tat and a rabbit anti-peptide antibody directed against amino acid residues 173–189 of Rex were used in this experiment as described in B. R. Cullen, J. Virol. 62 (1988) 2498–2501. Precipitated proteins were resolved on SDS/polyacrylamide gels and visualized by autoradiography.

The rex mutant genes encoded in the vectors pcRexM2, pcRexM7, pcRexM8, pcRexM14, pcRexM17 and pcRex13Δ15 yielded a negative phenotype for rex action in this assay system (see FIG. 2B, Lanes D, E, F, H, I and K) whereas controls (Lanes B and C) and other mutants (Lane G) yielded a positive phenotype.

All of these phenotypically negative Rex mutant clones are able to produce a Rex-specific protein recognized by the polyclonal anti-Rex antibody described above (FIG. 2A, Lanes C to E and G to I). In contrast, the mutation in clone pcRexM16 resulted in a protein undetectable by the Rex-specific antibody; this is believed to be due to a decreased protein half-life (not shown).

b) Transdominant repression of wild-type HIV-1 rev and/or HTLV-I rex function by pcRexM2, pcRexM7, pcRexM8, pcRexM13, pcRexM14, pcRexM17 and pcRex13Δ15.

The same experimental set-up was used to examine the ability of the rex mutants to inhibit in trans the function of the wild-type Rev and Rex protein. 0.25 μg of the genomic tat expression vector pgtat, 0.25 μg of the wild-type rev (pcRev) or the wild-type rex (pcRex) expression plasmid and an excess of each rex mutant expression plasmid (5 μg) were mixed separately and transfected into Cos cells. The influence of the mutants on the wild-type Rev or Rex function was measured by Tat-specific immunoprecipitation as described above.

The result of this experiment shows that the six rex mutants pcRexM2, pcRexM7, pcRexM8, pcRexM14, pcRexM17 and pcRex13Δ15 have the ability to inhibit the wild-type rex-mediated trans-activation (see FIG. 2C, Lanes C, D, E, G, H and I), that the four rex mutants pcRexM2, pcRexM7, pcRexM8 and (partially) pcRexM13 have the ability to inhibit the wild-type rev-mediated trans-activation (see FIG. 2D, Lanes C, D, E and F), while some of the mutants, namely, in this instance, pcRexM2, pcRexM7 and pcRexM8, are able to inhibit both the wild-type rex- and the wild-type rev-mediated trans-activation.

This set of experiments demonstrates on the protein level the transdominant repression of Rev and/or Rex function by the above rex mutants.

The results from Examples 1 to 3 also seem to indicate the existence of two functional domains in the HTLV-I Rex protein. Towards the amino terminus there are two mutants (pcRexM7, amino acid positions 58,59 and pcRexM8, amino acid positions 63,64) that are transdominant over both Rev and Rex proteins. A second cluster, containing mutants transdominant only over the Rex protein, is located in the middle of the coding sequence. The additional rev/rex transdominant mutant (pcRexM2, amino acid positions 30–32) located between the nuclear localization signal and the cluster comprised of mutants 7 and 8 could be part of a third functional domain or alternatively the introduced amino acid change might disturb the tertiary structure of the protein, resulting in the observed transdominant phenotype. 6.2.

Example 4

Clustered Point and Deletion Mutations in Rev

The Rev protein is phosphorylated at serine in vivo and is localized predominantly to the cell nucleus where it is concentrated in the nucleoli. The mutational analysis described below addresses, among other factors, the relevance of these properties to the function of Rev as a trans-activator of HIV-1 structural gene expression.

Clustered point mutations (pM) were introduced into the HXB-3 strain of HIV-1 Rev by, again, oligonucleotide directed mutagenesis, as described by Taylor et al., *Nucleic Acids Res.* 13 (1985) 8765–8785. Specifically, a bacteriophage M13 mutagenesis system (Amersham Corp., Arlington Heights, Ill., USA) was employed to introduce targeted nucleotide substitutions into full-length cDNA copies rev encoded by the expression vector pcREV (Malim et al., *Nature* 335 [1988] 181–183). The DNA and corresponding amino acid sequences of pcREV appear in FIG. 6.

A series of clustered point mutations were introduced into Rev (see M1–M14, FIG. 5), cloned, and their sequences confirmed using a dideoxynucleotide sequencing system (Stratagene, La Jolla, Calif., USA). The mutations were generally spaced evenly throughout Rev and served to target each of the 11 serine residues therein. The DNA sequence at and surrounding each mutation (pM1–pM14) are provided in FIG. 7, with the altered nucleotides being underlined.

Most of the noted mutations resulted in codons for aspartic acid (Asp) and leucine (Leu) replacing the residues "boxed" in FIG. 5. For ease of reference the mutations have been designated according to their location within Rev, e.g. pM1 being the most N-terminal mutation and pM14 the most C-terminal mutation.

While the precise structure of the various pM mutants is shown in FIG. 7, the majority of mutations affected only two codons. Exceptions to this generalization include M2, M4, M23, M24, and M25 which affected three codons and M6 which affected five codons. In most cases the amino acid substitutions arose from a two-amino acid missense mutation, however, in pM6, Asp and Leu replaced four arginine residues, thereby resulting in a two amino acid deletion, while both pM4 contains an additional adjacent single amino acid substitution not observed in the parental REV. Which the substitution involves the replacement of aspartic acid for tyrosine at position 23. These additional changes arose from single base errors in the single-stranded DNA oligonucleotide primer used in the mutagenesis protocol.

Most point mutations resulted in the formation of unique BglII sites, pM7 was constructed by the simple deletion of two adjacent serine residues (see FIG. 5). The BglII sites were all inserted in the same translational frame, thereby facilitating the subsequent construction of N-terminal and C-terminal deletion mutants (pΔ) of Rev. The pΔ mutants are designated by the location of deletion, e.g. pΔ11/14 has a deletion between the introduced pM11 and pM14 mutations.

Example 5

Expression of Rev Mutants

The parental cytomegalovirus immediate early promotor based vector pBC12/CMV (B. R. Cullen, *Cell* 46 [1986] 973–982) was used as a negative control. Also employed herein were the genomic tat gene expression vector pgTAT, and the secreted alkaline phosphatase gene expression vector pBC12/RSV/SEAP (Malim et al., supra, and Berger et al., *Gene* 66 [1988] 1–10, respectively).

The expression vector pcREV was modified to express the pM and pΔ rev mutants described herein. Again, a qualitative assay involving the co-transfection into COS cells of the modified pcREV together with pgTAT was used to assay the expression of HIV-1 rev and tat in the mutants (Malim et al., supra, and Malim et al., *Nature* 338 [1989] 254–57). Specifically, COS cell cultures (35 mm) were co-transfected by DNA-mediated transfections as described by Cullen (*Meth. Enzymol.* 152 [1987] 684–703) using 0.25 μg of pgTAT and 0.25 μg of the wild-type or a modified pcREV expression vector with DEAE-dextran and chloroquine.

Sixty hours post-transfection, the cultures were labelled with [$^{35}$S]-cysteine and [$^{32}$P]-inorganic phosphate ([$^{32}$P]-Pi) in parallel as described by Malim et al., 1988, supra, and Hauber et al., *J. Virol.* 62 [1988] 4801–04. The cells then were lysed with RIPA buffer and the relative level of rev and tat expression in the cultures assayed by immunoprecipitation analysis using rabbit polyclonal antipeptide antisera (Malim et al., [1988], supra, and Cullen et al., *J. Virol.* 62 [1988] 2498–2501). More specifically, antisera to Rev amino acid residues 1–20 (REV1/20) was used for immunoprecipitation of the mutant proteins encoded by pM5 and pM6, while antisera to Rev amino acid residues 27–51

(REV27/51) was used for immunoprecipitation of all remaining mutant proteins. Immunoprecipitation analysis of tat expression was performed using rabbit polyclonal antipeptide antisera to Tat amino acid residues 1–61 (TAT1/61).

The immunoprecipitated proteins were resolved by electrophoresis on 14% discontinuous SDS-acrylamide gels and visualized by autoradiography. The results of these experiments are depicted in FIG. 8, wherein the relative migration of known protein molecular weight markers is depicted to the right of the figure.

Immunoprecipitation of the [$^{35}$S]-cysteine and [$^{32}$P]-Pi labelled cultures with anti-Rev antisera are depicted in FIGS. 8A and 8C, respectively. Immunoprecipitation of the [$^{35}$S]-cysteine labelled cultures resulted in the majority of missense (pM) mutants yielding bands of an intensity and mobility comparable to the wild-type (FIG. 8A, lanes 1–14). Exceptions to this generalization include mutant pM6, which yielded an intense band of slightly faster mobility ($M_r$~18 kD) and pM1, which yielded a faint band of significantly slower mobility.

Immunoprecipitation analysis of tat expression using anti-Tat antisera provided a qualitative assay for rev function using pgTAT as a model indicator. As indicated above, absent rev, pgTAT expresses a fully spliced cytoplasmic tat mRNA which encodes the 86 amino acid (aa) two exon form of tat protein exclusively. In the presence of rev, however, pgTAT induces the cytoplasmic expression of an unspliced tat mRNA that encodes a truncated, one exon form of the protein 72 aa long.

Wild-type rev migrates at a relative molecular mass ($M_r$) of 19 kilodaltons (kD) and is readily detected in FIG. 8 (lane 0), while the 86 aa and the 72 aa forms of tat migrate at 15.5 kD and 14 kD, respectively. Mock-transfected cultures yield no specific signal under these assay conditions (Malim et al., 1988, supra), while inspection of FIG. 8B reveals that comparable levels of total tat protein were synthesized in both the cultures transfected with the mutant expression vectors and those co-transfected with the indicator construction pgTat. This suggests that none of the mutant Rev proteins were toxic to the transfected cells.

This analysis also demonstrates that 5 of the missense mutants and 2 of the deletion mutants of Rev were inactive (Lanes 4–7, 10, 16 and 20), while all other Rev mutants appeared fully able to induce 72 aa Tat expression. Four of the inactive missense mutations are clustered between amino acid residues 23 and 56 (M4 to M7), while the fifth inactive mutant (pM10) is separated by two fully functional mutants and affects residues 78 and 79. Deletion of either the 4 residues near the N-terminus (pΔ1/2) or the 21 residues near the C-terminus of Rev (pΔ11/14) had little or no effect on rev function. In contrast, deletion of additional sequences between residues 9 and 17 (pΔ1/3) resulted in loss of rev function.

Example 6

Trans-activation Capacity of Rev Mutants

In order to more rigorously evaluate the trans-activation capability of the rev mutants, their ability to rescue, in trans, a replication defective rev mutant of HIV-1 was tested. For purposes of this analysis, the rev HIV-1 provirus of vector pHIV-1Δrev (designated pHXB2Bam-p3 by Feinberg et al., Cell 46 [1986] 807–17) was used, which contains a frameshift mutation in the second coding exon of rev at amino acid 59 that renders the provirus incapable of replication, i.e., unable to produce a functional Rev protein when transfected into COS cells, absent co-transfection with a vector capable of expressing HIV-1 rev in trans (Rimsky et al., Nature 335 [1989] 738–40). The ability of the mutants to rescue the rev provirus was analyzed as depicted in FIG. 9, with viral replication being measured by quantitative assay of the level of HIV-1 p24 Gag protein (pg/ml) released into the culture supernatant using an ELISA assay system for soluble p24 Gag expression (DuPont-NEN Inc., Billerica, Mass., USA), with standard supplied by the manufacturer.

For purposes of control, transfection efficiency was monitored by co-transfection of the cultures with the Rev non-responsive vector pBC12/RSV/SEAP (12.5 ng/culture), a secreted alkaline phosphatase (SEAP) gene expression vector. Conveniently, SEAP levels were measured in parallel with supernatant p24 Gag levels. Additionally, some cultures were also co-transfected with 125 ng of either the negative control vector pBC12/CMV (NEG) or a wild-type rev gene expression vector (pcREV).

COS cells cultures (35 mm) were co-transfected with 250 ng of pHIV-1Δrev and 125 ng of a control vector or one of the modified mutant-containing vectors. Supernatant media were sampled 65 hours after transfection and assayed for p24 Gag protein expression levels. SEAP levels were measured in parallel. The resulting values are recited in FIG. 9, with correction for the slight variability observed in supernatant SEAP levels (with mean SEAP activity set at 1.00 units, the observed standards deviation was ±0.14 and the range 1.30 to 0.73).

Little variation in the supernatant level of SEAP activity was seen in this experiment, thus demonstrating equivalent transfection efficiency and confirming the lack of mutant induced cellular toxicity. Transfection of pHIV-1Δrev alone resulted in no detectable p24 Gag protein in the culture supernatant (Lane NEG), while co-transfection with a wild-type rev gene expression vector effectively complemented the ability of pHIV-1ΔRev to induce the secretion of p24 Gag (Lane pcREV).

Additionally, all Rev mutants testing positive in the pgTAT based assay visualized in FIG. 8B achieved a level of activity between 50 and 100% of that noted for the wild-type rev construction in rescue assay, with the exception of M1, which achieved −30% activity, a reduction which may reflect the decreased in vivo stability of the M1 mutant. All mutants that were scored as negative in FIG. 8B were fully negative in the rescue assay (i.e., ≦10 pg/ml of p24 Gag), with the exception of M7 which yielded a barely detectable level of supernatant p24 Gag protein.

Example 7

Rev Phosphorylation not Required for Biological Activity

The HIV-1 Rev protein is phosphorylated at one or more serine residues when expressed in vivo. The mutations delineated in FIG. 5 affect each of the 11 serine residues within the rev coding sequence. Thus, the immunoprecipitated [$^{32}$P]-Pi labelled Rev proteins transiently expressed in transfected COS cell cultures were monitored in order to identify the in vivo phosphorylation sites of the HIV-1 rev (FIG. 8C). A comparison of the level of [$^{32}$P]-Pi incorporation into rev with the level of [$^{35}$S]-cysteine incorporated in a culture transfected in parallel (FIG. 8A) was used to assess the effect of individual mutations on the level of phosphate incorporation. The results of this comparison are depicted in Table 1:

TABLE 1

Phenotypic analysis of HIV-1 rev gene mutants

| Clone | Rev[a] function | Phosphorylation[b] | Sub-cellular[c] localization | Trans-dominant[d] repression |
|---|---|---|---|---|
| wild-type | ++ | ++ | N | |
| M1 | + | ++ | ? | |
| M2 | ++ | + | N | |
| M3 | ++ | ++ | N > C | |
| M4 | – | ++ | N > C | – |
| M5 | – | ± | C > N | – |
| M6 | – | – | C > N | – |
| M7 | – | ++ | N > C | – |
| M8 | ++ | ++ | N > C | |
| M9 | ++ | ++ | N | |
| M10 | – | ++ | N | ++ |
| M11 | ++ | ++ | N | |
| M12 | ++ | + | N | |
| M13 | ++ | ++ | N | |
| M14 | ++ | ++ | N | |
| Δ1/2 | ++ | ± | N | |
| Δ1/3 | – | – | N > C | – |
| Δ9/14 | – | nd | nd | + |
| Δ10/14 | – | ± | N | + |
| Δ11/14 | ++ | ± | N | |
| Δ12/14 | ++ | ± | N | |
| Δ13/14 | ++ | ++ | N | |

[a]++, 50–100% wild-type (wt); +, 5–50% wt; –, <5% wt;
[b]++, comparable to wt; +, 30–60% wt; ±, 5–20% wt –, no detectable phosphorylation; nd, not done;
[c]?, not detected by immunofluorescence; nd, not done;
[d]++, highly trans-dominant; +, moderately trans-dominant; –, not detectably trans-dominant The analysis summarized in Table 1 identified four missense mutations which resulted in diminished phosphorylation. Of these, M2 and M12 had a moderate effect on phosphate incorporation (−30% and −60% inhibition, respectively) while M5 and M6 dramatically reduced the level of phosphate incorporation. The possible reasons for the dramatic effect of the M5 and M6 mutations (which do not affect any serine residues) on phosphorylation of rev will be discussed in more detail below.

To further localize the phosphate receptor serine residues in Rev, a study of the level of phosphorylation of the deletion mutants (pΔ) (FIG. 8C, lanes 15–20) was performed. This analysis revealed that the pΔ13/14 mutation was normally phosphorylated while the pΔ12/14 deletion, and the larger C-terminal deletions, displayed only a low level of phosphorylation (−90% inhibition). Similarly, the pΔ1/2 Rev mutant, which was effectively labelled with [$^{35}$S]-cysteine, also displayed a low level of [$^{32}$P]-Pi incorporation (−90% inhibition).

It is unclear why deletions that extend to the site of the M2 and M12 mutations had a more drastic effect on the level of phosphorylation than the missense mutations themselves. However, these results are consistent with the hypothesis that the Rev protein contains two primary sites of serine phosphorylation, one located at residue 8 (M2) and the second at residue 99 (M12). In any case, the mutants which lack these residues (i.e., pM2, pΔ1/2, pM12, pΔ12/14) display approximately wild-type levels of Rev activity (FIG. 8B, FIG. 9). It is therefore concluded that phosphorylation of Rev is not essential for the trans-activation function of the HIV-1 regulatory protein in transfected cells.

Example 8

Nuclear Localization of Rev

That the Rev protein is predominantly localized to the nuclei, particularly the nucleoli of expressing cells, was confirmed by analysis of the mutants using indirect immunofluorescence. The resulting phase contrast and corresponding immunofluorescence photographs of fixed, transfected COS cell cultures are shown in FIG. 10.

The technique of indirect immunofluorescence used to localize the Rev protein within the transfected COS cell was that described in B. R. Cullen, Meth. Enzymol. 152 [1987] 684 and B. R. Cullen, J. Virol. 62 [1988] 2498 except that a modified paraformaldehyde-based cell fixation procedure was employed (Ruben et al., J. Virol. 53 [1989] 1–8). Specifically, the cells were treated with rabbit polyclonal anti-Rev peptide antiserum followed by rhodamine conjugated goat anti-rabbit IgG.

The primary rabbit anti-Rev antibody was used at a 1:800 dilution. REV1/20 antibody was used for analysis of the majority of Rev mutants, with the exception of cultures transfected with the pM1, pM2, pM3, pΔ1/2 and pΔ1/3 vectors. REV27/51 antibody was used for these. The second antibody, rhodamine-conjugated goat anti-rabbit IgG (Boehringer Mannheim Biochemicals, Indianapolis, Ind., USA), was used at a 1:50 dilution.

The Rev mutants displayed four categories of subcellular localization as indicated in the Figure. The categories were: N, nuclear/nucleolar with no detectable cytoplasmic expression; N>C, slight cytoplasmic expression; N≧C, clear cytoplasmic expression with some nuclear concentration; C>N, random distribution within the cell. Representative examples of these distributions are shown in the Figure with the Rev proteins depicted being indicated in the upper right corner of the lower panel of pictures. The localization of each Rev mutant detected by this assay is set-forth in Table 1.

Figure 10A:
Figure 10C:
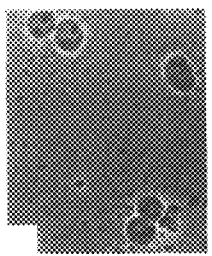
Figure 10E:
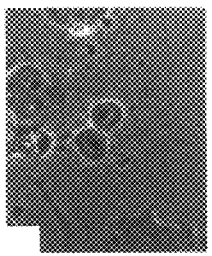
Figure 10G:
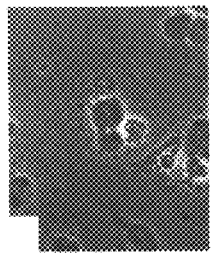
Figure 10I:
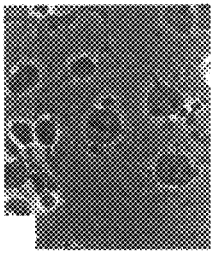
Figure 10B:
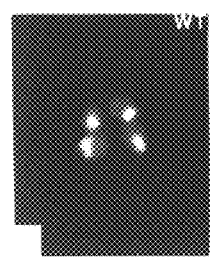
Figure 10D:
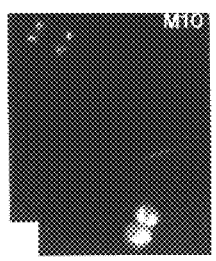
Figure 10F:
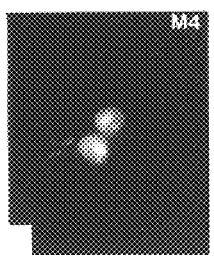
Figure 10H:
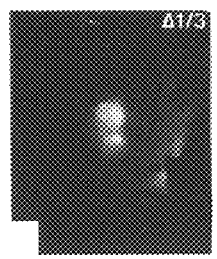
Figure 10J:
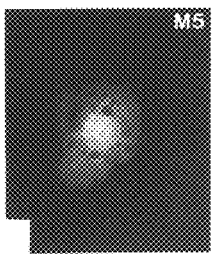

As shown, the majority of mutants displayed a fully wild-type subcellular localization (N), including the trans-activation negative clone pM10 (FIG. 10D). However, several mutants yielded a very low but detectable level of cytoplasmic fluorescence as typified by pM4 (FIG. 10F). This phenotype did not clearly correlate with biological activity, as both active mutants (pM3, pM8) and inactive mutants (pM4, pM7) displayed this property. Additionally, one fairly extensive deletion mutant, pΔ1/3, displayed a subcellular localization intermediate between the wild-type pattern and the pattern induced by mutations in the basic domain of Rev (N≧C, FIG. 10H). This deletion is, however, not located close to the basic domain. While the reason for this aberrant localization is unclear, it does correlate with the lack of biological activity observed for pΔ1/3.

Mutation of the arginine rich domain of Rev (pM5, pM6) which displays homology to known nuclear localization signals, resulted in a high level of cytoplasmic Rev protein (C>N). These proteins, however, were not excluded from the cell nucleus (FIG. 10J), suggesting that the basic domain of Rev is, in fact, a nuclear localization signal.

It is of interest to recall that pM5 and pM6 were not significantly phosphorylated in vivo despite retaining the sites proposed above as acceptors for phosphorylation. This may be because the kinase responsible for the phosphorylation of Rev is confined to the cell nucleus. Thus, it appears possible that inappropriate subcellular localization of the pM5 and pM6 Rev mutants is responsible for their low level of phosphorylation.

Example 9

Trans-dominant Repression of Rev Function

Rev mutants which had lost the ability to trans-activate HIV-1 structural gene expression were examined for their ability to inhibit in trans the function of the wild-type Rev protein.

COS cells (35 mm) were co-transfected with 250 ng of the indicator construction pgTAT and: 290 ng pBC12/CMV (negative control) (FIG. 11A, lane 1); 40 ng pcREV (low level), 250 ng pBC12/CMV (lane 2); 290 ng pcREV (high level) (lane 3); 40 ng pcREV, 250 ng pM4 (lane 4); 40 ng pcREV, 250 ng pM7 (Lane 5); 40 ng pcREV, 250 ng pM10 (lane 6). Sixty hours after transfection, the cultures were labelled with [$^{35}$S]-cysteine and subjected to immunoprecipitation analysis using rabbit anti-Tat antisera.

As shown in FIG. 11A, pM4 (lane 4) and pM7 (lane 5) had little effect on the activity of the wild-type Rev protein as measured by the induction of 72 aa Tat expression, whereas pM10 (lane 6) appeared to completely inhibit Rev function. This suggests that pM10 encodes a specific inhibitor of HIV-1 rev gene function.

In order to demonstrate that pM10 indeed acts by specifically preventing the cytoplasmic expression of the unspliced HIV-1 mRNA which encodes the 72 aa form of tat, the S1 nuclease protection assay of Malim et al., (1988), supra was employed. This assay (FIG. 11B) quantitates the level of spliced (S) and unspliced (U) tat mRNA expressed in the cytoplasm of COS cells (100 mm) transfected with: 2.75 μg pBC12/CMV+2.5 μg pcREV (Lane 1); 2.5 μg pgTAT+2.75 μg pBC12/CMV (Lane 2); 2.5 μg pgTAT+0.25 μg pcREV+2.5 μg pBC12/CMV (Lane 3); 2.5 μg pgTAT+ 2.75 μg pcREV (Lane 4); 2.5 μg pgTAT+0.25 μg pcREV+2.5 μg pM10 (Lane 5); 2.5 μg pgTAT+0.25 μg pcREV+2.5 μg pΔ10/14 (Lane 6). As shown, total input DNA was maintained at a total of 5.25 μg by inclusion of the parental expression vector pBC12/CMV as a negative control.

At 60 hours after transfection, cytoplasmic RNA was harvested for analysis and 5 μg aliquots were used in the S1 nuclease protection assay. The DNA probe used herein was a 798 base pair probe end-labelled at an XhoII site located within the first coding exon of tat using Klenow DNA polymerase (Malim et al. [1988] supra). The probe (I) was designed to quantitate the level of both unspliced (U) and spliced (S) cytoplasmic tat mRNA in the transfected COS culture. Using this probe, spliced (S) tat) mRNA is predicted to rescue a 202 nt probe fragment while unspliced (U) tat mRNA is predicted to rescue a 506 nt fragment. The relative level of unspliced RNA in each lane was quantitated by densitometry using an LKB soft laser scanner. The results, as visualized in FIG. 11B, are: Lane 2: 14% unspliced; Lane 3: 63% unspliced; Lane 4: 82% unspliced; Lane 5: 22% unspliced; Lane 6: 24% unspliced.

As expected spliced tat mRNA predominates in the cytoplasm of cells transfected with pgTAT alone (FIG. 11B, Lane 2) while unspliced tat mRNA is the dominant cytoplasmic species in the cytoplasm of cells that coexpress the HIV-1 Rev protein (FIG. 11B, Lanes 3 and 4). However, coexpression of pgTAT with both pcREV and pM10 restored the cytoplasmic predominance of the spliced form of tat mRNA (FIG. 11B, Lane 5).

Although the total level of RNA loaded in Lanes 5 and 6 appear somewhat low, it is thus nevertheless apparent that pM10 (Lane 5) was able to selectively inhibit the Rev induced cytoplasmic expression of unspliced tat MRNA from the pgTAT vector. Indeed, the relative level of unspliced tat mRNA detected in the presence of both pcREV and pM10 is comparable to the level observed in the absence of Rev.

The same pattern is apparent for pΔ10/14 (FIG. 11B, Lane 6). These results additionally demonstrate that a rev gene deletion extending 3' to the M10 mutation (pΔ10/14) also encodes a trans-repressor of Rev function. A more extensive deletion which extends through the site of the M10 mutation, termed pΔ9/14, also displayed a dominant negative phenotype (Table 1). However, a deletion which extended to the site of the M8 mutation was no longer trandominant (data not shown).

Example 10 pM10 Rev Mutant is a Competitive Inhibitor of Rev Function

The experimental results presented in FIGS. 11A and 11B demonstrate that pM10 can repress wild-type Rev function when present in trans. However, these experiments were performed in the presence of a large excess of pM10. To more accurately quantitate the effectiveness of the trans-inhibition of Rev function, the ability of increasing levels of pM10 to inhibit the rescue of the pHIV-1Δrev provirus mutant by a single level of pcREV was analyzed. This experiment also tested the effect of increasing levels of the pM4 and pΔ10/14 Rev mutants, as well as the effect of simply increasing the level of expression of wild-type Rev itself.

COS cell cultures (35 mm) were co-transfected with 25 ng of pHIV-1Δrev and 50 ng of pcREV, with an increasing fold molar excess of either pcREV (▼), pM4 (Δ), pΔ10/14 (o) or pM10 (■), as indicated in FIG. 12, i.e., 10 fold means co-transfection of 500 ng of the indicated plasmid construction. Total input DNA was maintained at a total of 587.5 ng by inclusion of the parental expression vector pBC12/CMV as a negative control. A SEAP gene expression vector was co-transfected as an internal control (12.5 ng/culture). The supernatant media were sampled at 65 hours and assayed by measurement of the level of supernatant p24 Gag expression.

The results of this assay are presented in FIG. 12 relative to the level of p24 expression obtained in the absence of any competing rev vector, a level defined as 1.00. All values are expressed relative to the p24 Gag expression level observed in the culture transfected with 25 ng pHIV-1Δrev, 50 ng pcREV, 12.5 ng pBC12/RSV/SEAP and 500 ng pBC12/ CMV. This control culture (●), which forms the basal value against which the competitive effects of the added Rev mutants were measured, was arbitrarily assigned a level of 1.00 unit of p24 Gag expression. The values presented herein are corrected for the slight variability observed in supernatant SEAP levels (mean SEAP activity was 1.00±0.27 with a range of 1.28 to 0.72).

As depicted, increasing the level of transfection of the wild-type rev expression vector pcREV was found to exert a mildly positive effect on viral replication, leading maximally to a –70% increase in the release of p24 Gag into the media. Co-transfection of the pM10 vector, in contrast, had a dramatically inhibitory effect on HIV-1 structural gene expression. The pattern of inhibition obtained is that expected for a competitive inhibitor of Rev function which displays the same affinity as wild-type Rev for its biological target. Thus, an equimolar amount of pM10 reduced p24 Gag expression –2 fold, a 2fold excess of pM10 reduced expression –3 fold, a 5fold excess –6 fold while a –10 fold excess reduced p24 Gag expression by –93%.

In addition to pM10, co-transfection of pΔ10/14 also reduced p24 Gag expression, however, this large deletion mutant of Rev was not as effective an inhibitor as pM10. It appears likely that the severely truncated protein expressed by pΔ10/14 is a less effective competitor because it lacks sequences which enhance the binding of Rev to its biological target.

Finally, co-transfection of pM4 also had an inhibitory effect, although it was slight, less than two fold (32%), at the maximum dose used. This effect is thought to arise from an activity (squelching) unrelated to RRE binding.

Example 11

Domain Structure of the HIV-1 Rev Trans-activator

As discussed above, transient gene expression analysis in transfected cells to assess the biological activity of a series of missense and deletion mutants of the HIV-1 trans-acting gene product Rev was used. These results evidence the possible existence of two functional domains within Rev, as depicted schematically in FIG. 12A, wherein S constitutes a splice site. Moreover, these two domains could be essential for trans-activation (cross-hatched).

The first of these domains (the RNA binding domain) defined by the four missense mutants pM4, pM5, pM6 and pM7, extends over about a 35 amino acid region between about amino acid position 10 and about amino acid position 68 of wild-type Rev and contains a highly basic sequence element which is essential for the nuclear localization of Rev. It also contains a nuclear localization (NL) signal (shaded). Mutants altered in this domain display a recessive negative phenotype.

In contrast, mutations within the second domain (the activation domain), which is centered approximately on amino acid residue 79, and defined i.a. by the missense mutant pM10 and the deletion mutants pΔ9/14 and pΔ10/14, also result in a loss of Rev function but, remarkably, the negative phenotype displayed by these mutants is trans-dominant. Two regions of Rev (hatched in FIG. 12A) appear to be dispensable for protein function. As depicted herein, mutations in the Rev activation domain render Rev defective and result in the production of proteins which competitively inhibit wild-type Rev function. This trans-repression is sufficient to markedly reduce or suppress the replication of HIV-1 in transfected cells. The molecular basis for the dominant negative phenotypes displayed by pM10 and the related deletion mutants is not known yet. However, the observation that both missense (M10) and deletion (Δ9/14, Δ10/14) mutants are able to inhibit Rev function in trans does suggest that the loss, rather than the acquisition, of an attribute is responsible. One possibility is that defective Rev protein molecules might be able to form mixed multimers with wild-type Rev protein subunits and hence inhibit the function of the wild-type protein in a transdominant manner. It is not, however, currently known whether Rev functions as a monomer or as a multimer in vivo. An alternative hypothesis, based on earlier work involving the functional dissection of a number of prokaryotic and eukaryotic transcription factors, is that transcriptional trans-activators bear two distinct functional domains, a specific "binding domain" that directs the protein to its appropriate target substrate, and an "activation domain" that permits the functional consequence of the binding event, in this case transcriptional activation, to be displayed. In several systems, the binding domain has been shown to consist of a sequence-specific DNA binding element; however, in at least one case, that of the herpes simplex virus type 1 (HSV-1) trans-activator VP16, it appears that the binding domain instead mediates a specific interaction with a cellular transcription factor which in turn binds to target sequences in the HSV-1 genome. Importantly, mutation of the binding domain tends to result in a negative phenotype which is recessive at moderate levels of expression. In contrast, mutation or deletion of the activating domain of a transcription factor may result in mutants with a dominant negative phenotype. These mutants, which retain an intact binding domain, are believed to compete with the wild-type trans-activator for binding to the appropriate cellular target, yet are incapable of activating transcription once binding has occurred. In the case of the HSV-1 VP16 protein, overexpression of such a transdominant mutant has been shown to inhibit wild-type VP16 function effectively, and hence to preclude replication of HSV-1 in normally permissive cells.

Although the rev gene product is a posttranscriptional trans-regulator of gene expression it appears reasonable that the concept of two distinct functional domains should also be applicable in this case. In particular, Rev functions in a highly sequence-specific manner, via a direct interaction (M. H. Malim et al., *Cell* 60 [1990] 675–683) with its RNA target sequence, the RRE, and must therefore contain sequences that confer this specificity. Once binding has occurred, this event must be translated into an activation event, in this case nuclear export of the incompletely spliced RNAs that encode the HIV-1 structural proteins. Mutations in this latter domain might thus result in competitive inhibitors of wild-type Rev function. This is the phenotype observed for the pM10 and pΔ10/14 mutants of Rev and these mutants may indicate the existence of a discrete activation domain. Conversely, the second, more N-terminal essential region of the Rev protein defined by this mutational analysis may serve the same function as the "binding domains" defined in several transcription factors. Mutants altered in this domain (e.g., pM4, pM7) do in fact display a generally recessive negative phenotype, although a low but significant inhibition is observed at high expression levels. Further transdominant mutants have also been found (see FIG. 5A and Examples 11a and 11b) which allow the localization of the Rev activation domain to be refined as extending from about amino acid position 68 to about amino acid position 90, particularly from about position 78 to about position 86 and especially from about position 78 to about position 83 or 84 of wild-type Rev.

Example 11a

Further Transdominant HIV-1 Rev Mutants

Further HIV-1 rev mutants have been prepared analogously to the procedures described above under 6.2. They are designated and characterized as appears in FIG. 5A and in Table 2. The in vivo phenotype has been determined according to M. H. Malim et al., *Cell* 58 [1989] 205–214 (all assays were internally controlled for transfection efficiencies).

In addition to those found as described under Examples 4 to 11 above, the following further mutants have been found to transdominantly inhibit the wild-type HIV-1 Rev function: pM21, pM22, pM27, pM28, pM29 and pM32.

TABLE 2

Phenotypic analysis of further HIV-1 rev gene mutants

| Clone | Phenotype[a] | Transdominant repression[b] |
|---|---|---|
| pBC12/CMV (vector alone) | | 0 |
| pM15 | ++ | |
| pM16 | ++ | |
| pM17 | ++ | |
| pM18 | + | |
| pM19 | ++ | |
| pM20 | ++ | |

TABLE 2-continued

Phenotypic analysis of further HIV-1 rev gene mutants

| Clone | Phenotype[a] | Transdominant repression[b] |
|---|---|---|
| pM21 | − | 97 |
| pM22 | − | 93 |
| pM23 | ++ | |
| pM24 | ++ | |
| pM25 | ++ | |
| pΔ9/19 | − | |
| pΔ18/19 | + | |
| pΔ18/23 | − | |
| pΔ22/14 | − | |
| pΔ23/14 | + | |
| pM27 | − | 92 |
| pM28 | − | 92 |
| pM29 | − | 91 |
| pM32 | − | 97 |
| pM33 | ++ | |
| pM34 | ++ | |
| pM35 | ++ | |
| pM36 | + | |

[a] ++ 40–100% (relative to wild-type Rev activity)
+ 5–39%
− <5%
[b] as % inhibition of wild-type Rev function, with a 10fold excess of mutant Rev over wild-type Rev Example 11b Effect on HIV-2 and SIV Rev Function The multivalent potential of the transdominant HIV-1 rev gene mutants of Example 4 to 11 has been analyzed using the methodology already described above under 6.2. and in M. H. Malim et al., Proc.Natl.Acad.Sci.USA 86 [1989] 8222–8226. The results obtained show that at least mutant pM10 has the capability of transdominantly inhibiting not only the phenotypic expression of the HIV-1 rev gene, but additionally also HIV-2 rev and $SIV_{mac}$ rev gene function, as shown, e.g. for HIV-2 rev, by strong inhibition of HIV-2 Rev function when an excess of pM10 is expressed together with wild-type HIV-2 rev gene, through inhibition of unspliced MRNA and of 1-exon tat expression in the cytoplasm. 6.3.

Example 12

Analyses of Rex Function

For testing rex mutants for Rex function (FIG. 14), each mutant DNA was cotransfected with pgTAX-LTR into COS cells using DEAE-dextran (B. P. Cullen, Meth. Enzymol. 152 [1987] 692–693). All plasmids were added at a concentration of 1.25 μg/ml. Forty-eight hours after transfection, the cells were metabolically labelled with $^{35}$S-cysteine for 2 hours, cellular extracts prepared, and the samples were immunoprecipitated with the 0.5 alpha human monoclonal antibody that specifically reacts with the HTLV-I envelope protein. Immunoprecipitates were analyzed on SDS-10% polyacrylamide gels.

For simultaneous analysis of HTLV-I Env, Tax and Rex protein production (FIG. 15), COS cells were cotransfected with pgTAX-LTR (0.1 μg/ml) and the vectors encoding the mutant Rex proteins (1 μg/ml) or the wild-type pREX, pREV and pCMV-IL-2 vectors (1 μg/ml). Immunoprecipitation analyses of HTLV-I proteins used the following antibodies: Env, 0.5 alpha antibody; Tax, Tax-specific anti-peptide rabbit antisera (prepared by one of the inventors; can also be prepared according to W. Wachsman et al., Science 235 [1987] 674–677); Rex, Rex-specific anti-peptide rabbit antisera (prepared by one of the inventors; can also be prepared according to H. Siemi et al., Cell 55 [1988] 197–209). In each case, the radiolabeled cellular extract was used for the three immunoprecipitations and electrophoretic analyses; only the relevant region of each of the resultant autoradiograms is presented in each panel of FIG. 15.

For subcellular localization of HTLV-I Rex mutants by immunofluorescence (FIG. 16), COS cells were transfected with the indicated expression plasmids and fixed with paraformaldehyde 48 hours later. The cells were then sequentially stained with rabbit ant-Rex peptide antiserum (1:100 dilution) and goat anti-rabbit IgG conjugated to rhodamine as previously described (B. R. Cullen [1987] supra).

Example 13

Inhibition of Rex and Rev Function

For analysis of the ability of rex mutants to inhibit function of the wild-type Rex protein (FIG. 17A), COS cultures were cotransfected with three plasmids including pgTAX-LTR (1.25 μg/ml), pREX (0.1 μg/ml) and 1 μg/ml of the Rex mutants (Lanes 1–6), pREX (Lane 7), pREV (Lane 8) or pCMV-IL-2 (Lane 9). Env production was analyzed by immunoprecipitation with the 0.5 alpha monoclonal antibody and electrophoresis through SDS-10% polyacrylamide gels. For analysis of inhibition of the function of HIV-1 Rev protein, COS cells were cotransfected with pgTAT, pREV and a 10-fold molar excess of pBC/CMV-IL-2 or the M6, M7 and M13 transdominant Rex mutants. After 48 hours of culture and biosynthetic labeling with $^{35}$S-cysteine, cellular extracts were assayed by immunoprecipitation for Rev-induced production of the truncated 72 amino acid form of the Tat protein (Lane 2). At a 10:1 molar ratio, the M6, M7 and M13 (Lanes 3–5) mutants completely inhibited the action of the HIV-1 Rev protein as only the full-length 86 amino acid form of the Tat protein was detected. For analysis of inhibition of replication of HIV-1, COS cells were cotransfected with the rev-deficient HIV-1 proviral plasmid pHXB2-Bam-p3 (M. R. Feinberg et al., Cell 46 [1986] 807–817) and pREX in the presence of the indicated fold excess of the M1, M6, M7, and M13 mutants. Total DNA concentration in the transfection cocktail was maintained at a constant level by the addition of varying amounts of the pBC/CMV-IL-2 parental vector. Three days after transfection, supernatant levels of the HIV-1 p24 Gag protein were measured by ELISA (Coulter Immunology kit). The M6, M7 and M13 mutants produced dose-related inhibition of HIV-1 p24 production while the recessive negative M1 mutant did not.

7. Pharmacological Aspects

HIV-1 is the predominant etiologic agent of AIDS; HTLV-I is causing i.a. ATL; HTLV-II is etiologically related to some cases of variant T-cell hairy cell leukemia. The HIV-1 Rev and the HTLV-I Rex trans-activators have been shown to be essential for viral replication in culture and Rev and Rex are therefore potential targets for chemotherapeutic intervention in afflicted patients.

Described herein are mutant forms of Rev and/or Rex that act as effective competitive inhibitors of wild-type Rev and/or Rex function in cells transfected with wild-type Rev or Rex and which, therefore, also function as effective inhibitors of HIV-1 and/or HTLV-I and/or HTLV-II replication. These mutants could thus be used to protect the lymphoid cells of patients exposed to infection. An indication that this approach can be expected to be practicable is the observation that expression of an analogous transdominant derivative of the essential VP16 trans-activator of HSV-1 can effectively confer resistance to HSV-1 infection on a normally susceptible cell population (A. D. Friedman et al., *Nature* 335 [1988] 452–454). Further, corresponding transgenic mice appear to be immune to infection with HSV-1.

Mutant rex and rev genes encoding transdominant repressors of Rex or Rev are thus indicated for use as "intracellular immunogens" for the treatment of diseases caused by HTLV-I or by HTLV-II or, respectively, of HIV-1-induced diseases including AIDS and ARS (ARC). Further, since at least some of the transdominant Rex mutant proteins of the invention have the particular attribute of being able to inhibit both HTLV-I Rex and HIV-1 Rev protein action, they are thus indicated for use in the treatment of infections by both virus types. This property may be of particular value in patients coinfected with more than one of these viral pathogens or in those whose infection has not been distinguished between these two agents.

The existence of therapeutic agents effective on more than one viral species appears to have been nowhere disclosed prior to the present invention. In view of its broad applicability the above concept appears to be indicated not only in the therapy of the diseases caused by viral species encoding Rev and Rex but also in further viral diseases caused by organisms having genes similarly regulated.

The invention is thus indicated for use in the prophylaxy and therapy of viral, particularly retroviral, diseases such as ATL (adult T-cell leukemia), AIDS (acquired immunodeficiency syndrome), ARS or ARC (AIDS-related syndrome or complex), SIV (simian immunodeficiency virus) such as $SIV_{mac}$, FIV (feline immunodeficiency virus), EIAV (equine infectious anemia virus), visna virus and bovine immunodeficiency virus infections, especially human retroviral diseases, more especially human retroviral diseases caused by pathogens regulated by the rex or rev gene or equivalents thereof, such as ATL, AIDS and ARS (ARC).

Of particular benefit is thereby the multivalent aspect of the repressor effect since it is of advantage in the treatment of multiple, especially double infection by virus, such as is often seen in i.v. drug users coinfected by HIV-1 and HTLV-I, or in treatment in situations of single infection with increased risk of further infection, such as in HIV infection, or in prophylaxy in situations where it is desired to protect against infection by a spectrum of different viral species.

This multivalent aspect, while normally expected to be most effective in the inhibition of somewhat related viruses of one particular type, e.g. retroviral viruses, is not necessarily restricted to closely related viruses, such as either DNA virus or RNA (retro-)virus: interactions are known to exist in levels of infectivity between DNA viruses and retroviruses, such as between HIV-1 and JC virus, a human papovavirus (H. Gendelman et al., *Proc.Natl.Acad.Sci.USA* 83[1986]9759–9763; H. Tada et al., ibid. 87 [1990] 3479–3483) and common regulatory mechanisms may thus well be at work in phylogenically more distant viral species on which the above principles of multivalent transdominancy could be applied.

The therapeutic potential of the invention is immediately apparent, since the repression of e.g. the Rex function of HTLV-I and the Rev function of HIV-1 blocks viral replication, thus preventing the formation of infective virus particles, and is thus expected to perpetuate the latent stage of infection. Thus the cells of subjects already infected with the HIV-1 virus but also having, integrated into their genome, the gene for a transdominant repressor would remain functional and the subjects indefinitely free of symptoms of disease, without the need for long-term therapy.

Viewed in this light the genes according to the invention are pharmaceuticals in themselves, for single or multiple administration either directly in vivo or indirectly in vitro, preferably as part of a vector, e.g. a retroviral or plasmid vector, in a form suitable for achieving delivery in a functional form into target mammalian cells; for example insertion of genes that encode such transdominant inhibitors of viral replication may be effected in vitro into cells of patients by direct implantation into the genome of lymphoid cells derived from infected individuals and these cells may be administered to the donor patient after insertion has been effected. Since HTLV-I and HTLV-II as well as HIV-1 replicate in various types of T-cells, the diseases they cause would appear to be particularly suited.

One application of this would thus parallel the gene therapy concept disclosed in e.g. T. Friedmann, *Science* 244 (Jun. 16, 1989) 1275 or P. M. Lehn, *Bone Marrow Transplant* 1 (1987) 243: hematopoietic stem cells are extracted from e.g. AIDS/ATL patients and cultivated in vitro, the mutated gene according to the invention, coding for a transdominant repressor for the function to be repressed, such as the Rev/Rex function, is implanted into these cells using retroviral vectors; the now viral-resistant progeny-producing stem cells are returned to the immune system of the original patient, where they are expected to proliferate in view of their acquired selective advantage over non-treated stem cells; in due time the population of hematopoietic cells will consist entirely of cells producing the transdominant factor and be virus-resistant.

Methods on how to effect this are already known in the art, see e.g. U.S. Pat. No. 4,868,116. Vectors, e.g. retroviral or plasmid vectors, for delivering the mutated genes according to the invention into target mammalian cells such as bone marrow cells are disclosed or referred to in, e.g., *Science* 244 (Jun. 16, 1989) 1275. Thus, for example, various Rev and/or Rex transdominant genes are cloned into retroviral vector systems. After retroviral-mediated gene delivery into e.g. HIV-infected human cell lines the inhibitory effect of the transdominant mutants is readily ascertained by inhibition of viral production.

The above therapeutic concept is an example of intracellular immunization as envisaged in D. Baltimore, *Nature* 335 (1988) 395. In brief, the concept involves insertion of a gene that encodes a repressor of some vital function of a selected virus into the particular target cells which that virus infects (e.g., certain T-cells in the case of the virus causing AIDS). Application of this approach to therapy with a transdominant repressor of any virus is conditional upon establishment that potential vectors for genes encoding such mutant proteins and possible methods of inserting these vectors into the proper cells, which have been identified in model systems, constitute effective and safe intracellular delivery systems for human or animal applications. The concept can thus be put to the test of experimental verification only with difficulty in view of the ethical barriers presently preventing gene therapy. However the first such genetic experiments have just started, with non-therapeutic goals. It is to be expected that very shortly after the innocuity of the procedure has been demonstrated these pioneer experiments will be followed by similar trials with therapeutic goals, first in life-threatening conditions such as AIDS disease, and the present invention would appear to be well suited for early use in such trials (see T. Friedmann, *Science* 244 [Jun. 16, 1989] 1279, second column, "Infectious diseases").

A further mode of using the invention includes insertion not of a gene but of a repressor protein according to the invention into target cells. Administration e.g. orally or parenterally is effected in conventional manner in a form allowing intracellular penetration, such as by liposome-mediated delivery.

For these uses the exact dosage will of course vary depending upon the compound employed, mode of administration and treatment desired; ascertaining the most suitable dosage in a particular situation is within the skill of the man of the art.

The invention is further indicated for use in the design and engineering of anti-viral drugs based on transdominancy. A means has now been found for manipulating viral gene function which appears to be of general applicability for several viral species, although the structural basis therefor varies widely in the various viruses. This unexpected finding opens the way for studies aimed at designing further specific, possibly low molecular weight, possibly non-peptidic transdominant inhibitors of viral replication, in particular the design of inhibitors able to mimic the transdominant, i.e. primarily the RNA-binding domain in the mutant Rev or Rex proteins, such as low molecular weight inhibitors or neutralizing monoclonal antibodies.

It is to be understood that various combinations or changes in form and detail can be made to the invention as described above without departing from the scope of the present invention.

It is also to be understood that further mutants as described above, including mutants among the specific mutants already constructed and disclosed herein but which have not been characterized but may be characterized upon more detailed investigation as being transdominantly inhibitory and/or multivalent, and further mutants in accordance with the principles described above but not specifically disclosed herein, also fall within the scope of the present invention.

What is claimed is:

1. A mutant Rev protein which transdominantly represses the phenotypic expression of the wild-type rev gene of HIV-1, which protein comprises one or more mutations from amino acid position 68 to amino acid position 90 of the wild-type Rev protein of HIV-1.

2. A mutant Rev protein according to claim 1 wherein the mutations are missense or deletion mutations.

3. A mutant Rev protein according to claim 2 wherein the mutations are missense mutations.

4. A mutant Rev protein according to claim 3 comprising mutations at amino acid positions 78 and 79 of the wild-type Rev protein of HIV-1.

5. A composition comprising a mutant Rev protein according to claim 4 and a carrier or diluent.

6. A mutant Rev protein according to claim 1 comprising Asp at position 78 and Leu at position 79 of the wild-type Rev protein of HIV-1.

7. A mutant Rev protein which transdominantly represses the phenotypic expression of the wild-type rev gene of HIV-1, which mutant HIV-1 Rev protein comprises a first domain having substantially the specific binding functions of the wild-type HIV-1 Rev, and a second domain not having the activation functions of said wild-type HIV-1 Rev, said second domain comprising from about amino acid 68 to about amino acid 90 of the wild-type HIV Rev-1 protein, said second domain being modified by comprising one or more mutations.

8. A mutant Rev protein according to claim 7 wherein the mutations are missense or deletion mutations.

9. A mutant Rev protein according to claim 8 wherein the mutations are missense mutations.

10. A mutant Rev protein according to claim 7 comprising mutations at amino acid positions 78 and 79 of the wild-type Rev protein of HIV-1.

11. A mutant Rev protein according to claim 10 comprising Asp at position 78 and Leu at position 79 of the wild-type Rev protein of HIV-1.

12. A composition comprising a mutant Rev protein according to claim 7 and a carrier or diluent.

13. A mutant HIV-1 Rev protein which transdominantly represses the phenotypic expression of the wild-type rev gene of HIV-1, which mutant HIV-1 Rev protein comprises a first domain and a second domain, the first domain comprising from about amino acid 10 to about amino acid 68 of the wild-type HIV-1 Rev protein and the second domain comprising from about amino acid 68 to about amino acid 90 of the wild-type HIV Rev-1 protein, said second domain being modified by comprising one or more mutations.

14. A mutant Rev protein according to claim 13 wherein the mutations are missense or deletion mutations.

15. A mutant Rev protein according to claim 14 wherein the mutations are missense mutations.

16. A mutant Rev protein according to claim 13 comprising Asp at position 78 and Leu at position 79 of the wild-type Rev protein of HIV-1.

17. A mutant Rev protein according to claim 13 selected from the group consisting of mutant proteins M10, Δ9/14, and Δ10/14.

18. A composition comprising a mutant Rev protein according to claim 13 and a carrier or diluent.

19. Mutant Rev protein M10.

20. A composition comprising a mutant Rev protein according to claim 19 and a carrier or diluent.

* * * * *